(12) United States Patent
Lipman et al.

(10) Patent No.: US 10,330,667 B2
(45) Date of Patent: Jun. 25, 2019

(54) ANALYTE MONITORING METHODS AND SYSTEMS

(75) Inventors: Kelley J. Lipman, Livermore, CA (US); Robin S. Gaffney, Redwood City, CA (US); Kimberly J. Tansey, San Carlos, CA (US)

(73) Assignee: Intuity Medical, Inc., Fremont, CA (US)

( * ) Notice: Subject to any disclaimer, the term of this patent is extended or adjusted under 35 U.S.C. 154(b) by 0 days.

(21) Appl. No.: 13/168,644

(22) Filed: Jun. 24, 2011

(65) Prior Publication Data

US 2012/0166090 A1    Jun. 28, 2012

Related U.S. Application Data

(60) Provisional application No. 61/358,825, filed on Jun. 25, 2010.

(51) Int. Cl.
| | |
|---|---|
| *G01N 33/48* | (2006.01) |
| *G01N 33/487* | (2006.01) |
| *A61B 5/15* | (2006.01) |
| *A61B 5/157* | (2006.01) |
| *G16H 40/63* | (2018.01) |

(Continued)

(52) U.S. Cl.
CPC ....... *G01N 33/48792* (2013.01); *A61B 5/157* (2013.01); *A61B 5/150022* (2013.01); *A61B 5/150358* (2013.01); *G06F 19/00* (2013.01); *G16H 40/63* (2018.01); *A61B 5/14532* (2013.01); *A61B 5/151* (2013.01);

(Continued)

(58) Field of Classification Search
CPC ............ A61K 2300/00; A61K 31/4745; A61K 31/435; A61K 31/4375; G07F 17/3244; G07F 17/3239; G07F 17/3232; G07F 17/3269

See application file for complete search history.

(56) References Cited

U.S. PATENT DOCUMENTS

| 842,690 A | 1/1907 | Oswalt |
|---|---|---|
| D137,874 S | 5/1944 | Partridge |

(Continued)

FOREIGN PATENT DOCUMENTS

| CA | 2 201 530 A1 | 9/1997 |
|---|---|---|
| CA | 2 513 465 A1 | 8/2004 |

(Continued)

OTHER PUBLICATIONS

ADA Consensus Development Panel. (Jan.-Feb. 1987). "Consensus Statement on Self-Monitoring of Blood Glucose," *Diabetes Care* 10(1):95-99.

(Continued)

*Primary Examiner* — Larry D Riggs, II
(74) *Attorney, Agent, or Firm* — Cooley LLP

(57) ABSTRACT

A method is disclosed involving monitoring the concentration of at least one target analyte in a sample of body fluid using a meter, the meter including a user interface, the method including: obtaining a sample of body fluid; testing the sample to determine the concentration of the at least one target analyte contained therein; and presenting the user with a reminder to associate the test with an appropriate time corresponding to before or after a particular meal using the user interface. Associated devices, systems and arrangements are also disclosed.

36 Claims, 3 Drawing Sheets

(51) Int. Cl.
*G06F 19/00* (2018.01)
*A61B 5/145* (2006.01)
*A61B 5/151* (2006.01)
*A61B 5/00* (2006.01)

(52) U.S. Cl.
CPC ......... *A61B 5/15186* (2013.01); *A61B 5/7475* (2013.01); *G06F 19/3456* (2013.01)

(56) References Cited

U.S. PATENT DOCUMENTS

| | | |
|---|---|---|
| 2,749,797 A | 3/1950 | Harks |
| 3,092,465 A | 6/1963 | Adams, Jr. |
| 3,310,002 A | 3/1967 | Wilburn |
| 3,620,209 A | 11/1971 | Kravitz |
| 3,623,475 A | 11/1971 | Sanz et al. |
| 3,626,929 A | 12/1971 | Sanz et al. |
| 3,630,957 A | 12/1971 | Rey |
| D223,165 S | 3/1972 | Komendat |
| 3,723,064 A | 3/1973 | Liotta |
| 3,741,197 A | 6/1973 | Sanz et al. |
| 3,961,898 A | 6/1976 | Neeley et al. |
| 3,992,158 A | 11/1976 | Przybylowicz et al. |
| 4,014,328 A | 3/1977 | Cluff et al. |
| 4,042,335 A | 8/1977 | Clement |
| 4,057,394 A | 11/1977 | Genshaw |
| 4,109,655 A | 8/1978 | Chacornac |
| 4,250,257 A | 2/1981 | Lee et al. |
| 4,253,083 A | 2/1981 | Imamura |
| 4,254,083 A | 3/1981 | Columbus |
| 4,258,001 A | 3/1981 | Pierce et al. |
| 4,260,257 A | 4/1981 | Neeley et al. |
| 4,289,459 A | 9/1981 | Neeley et al. |
| 4,321,397 A | 3/1982 | Nix et al. |
| 4,350,762 A | 9/1982 | DeLuca et al. |
| 4,394,512 A | 7/1983 | Batz |
| 4,414,975 A | 11/1983 | Ryder et al. |
| 4,416,279 A | 11/1983 | Lindner et al. |
| 4,418,037 A | 11/1983 | Katsuyama et al. |
| 4,422,941 A | 12/1983 | Vaughan, Jr. et al. |
| 4,429,700 A | 2/1984 | Thees et al. |
| 4,627,445 A | 12/1986 | Garcia et al. |
| 4,637,403 A | 1/1987 | Garcia et al. |
| 4,637,406 A | 1/1987 | Guinn et al. |
| 4,653,513 A | 3/1987 | Dombrowski |
| 4,661,319 A | 4/1987 | Lape |
| 4,702,261 A | 10/1987 | Cornell et al. |
| 4,711,250 A | 12/1987 | Gilbaugh, Jr. et al. |
| 4,737,458 A | 4/1988 | Batz et al. |
| 4,767,415 A | 8/1988 | Duffy |
| 4,774,192 A | 9/1988 | Terminiello et al. |
| 4,787,398 A | 11/1988 | Garcia et al. |
| 4,790,979 A | 12/1988 | Terminiello et al. |
| 4,794,926 A | 1/1989 | Munsch et al. |
| 4,815,843 A | 3/1989 | Tiefenthaler et al. |
| 4,829,470 A | 5/1989 | Wang |
| 4,844,095 A | 7/1989 | Chiodo et al. |
| 4,846,785 A | 7/1989 | Cassou et al. |
| 4,887,306 A | 12/1989 | Hwang et al. |
| 4,920,977 A | 5/1990 | Haynes |
| 4,929,426 A | 5/1990 | Bodai et al. |
| 4,930,525 A | 6/1990 | Palestrant |
| 4,935,346 A | 6/1990 | Phillips |
| 4,953,552 A | 9/1990 | De Marzo |
| 4,966,646 A | 10/1990 | Zdeblick |
| 4,983,178 A | 1/1991 | Schnell |
| 4,995,402 A | 2/1991 | Smith |
| 5,029,583 A | 7/1991 | Meserol |
| 5,035,704 A | 7/1991 | Lambert et al. |
| 5,049,487 A | 9/1991 | Phillips et al. |
| 5,050,617 A | 9/1991 | Columbus et al. |
| 5,059,394 A | 10/1991 | Phillips et al. |
| 5,077,199 A | 12/1991 | Basagni et al. |
| 5,094,943 A | 3/1992 | Siedel et al. |
| 5,110,724 A | 5/1992 | Hewett |
| 5,114,350 A | 5/1992 | Hewett |
| 5,116,759 A | 5/1992 | Klainer et al. |
| 5,131,404 A | 7/1992 | Neeley et al. |
| 5,141,868 A | 8/1992 | Shanks et al. |
| 5,145,565 A | 9/1992 | Kater et al. |
| 5,146,437 A | 9/1992 | Boucheron |
| 5,153,416 A | 10/1992 | Neeley |
| 5,164,575 A | 11/1992 | Neeley et al. |
| 5,166,498 A | 11/1992 | Neeley |
| 5,174,291 A | 12/1992 | Schoonen et al. |
| 5,176,632 A | 1/1993 | Bernardi |
| 5,179,005 A | 1/1993 | Phillips et al. |
| 5,183,741 A | 2/1993 | Arai et al. |
| 5,196,302 A | 3/1993 | Kidwell |
| 5,208,163 A | 5/1993 | Charlton et al. |
| 5,213,966 A | 5/1993 | Vuorinen et al. |
| 5,217,480 A | 6/1993 | Habar et al. |
| 5,218,966 A | 6/1993 | Yamasawa |
| 5,223,219 A | 6/1993 | Subramanian et al. |
| 5,228,972 A | 7/1993 | Osaka et al. |
| 5,234,818 A | 8/1993 | Zimmermann et al. |
| 5,241,969 A | 9/1993 | Carson et al. |
| 5,251,126 A | 10/1993 | Kahn et al. |
| D341,848 S | 11/1993 | Bigelow et al. |
| 5,269,800 A | 12/1993 | Davis, Jr. |
| 5,275,159 A | 1/1994 | Griebel |
| 5,278,079 A | 1/1994 | Gubinski et al. |
| 5,279,294 A | 1/1994 | Anderson et al. |
| 5,288,646 A | 2/1994 | Lundsgaard et al. |
| 5,299,571 A | 4/1994 | Mastrototaro |
| 5,301,686 A | 4/1994 | Newman |
| 5,302,513 A | 4/1994 | Mike et al. |
| 5,304,468 A | 4/1994 | Phillips et al. |
| 5,306,623 A | 4/1994 | Kiser et al. |
| 5,308,767 A | 5/1994 | Terashima |
| 5,314,441 A | 5/1994 | Cusack et al. |
| 5,320,607 A | 6/1994 | Ishibashi |
| 5,354,537 A | 10/1994 | Moreno |
| 5,360,595 A | 11/1994 | Bell et al. |
| 5,368,047 A | 11/1994 | Suzuki et al. |
| 5,383,512 A | 1/1995 | Jarvis |
| 5,390,671 A | 2/1995 | Lord et al. |
| 5,395,388 A | 3/1995 | Schraga |
| 5,399,316 A | 3/1995 | Yamada |
| 5,401,110 A | 3/1995 | Neeley |
| 5,402,798 A | 4/1995 | Swierczek et al. |
| 5,426,032 A | 6/1995 | Phillips et al. |
| 5,441,513 A | 8/1995 | Roth |
| 5,451,350 A | 9/1995 | Macho et al. |
| 5,458,140 A | 10/1995 | Eppstein et al. |
| 5,460,777 A | 10/1995 | Kitajima et al. |
| 5,460,968 A | 10/1995 | Yoshida et al. |
| 5,482,473 A | 1/1996 | Lord et al. |
| 5,506,200 A | 4/1996 | Hirschkoff et al. |
| 5,507,288 A | 4/1996 | Böcker et al. |
| 5,508,200 A | 4/1996 | Tiffany et al. |
| 5,510,266 A | 4/1996 | Bonner et al. |
| 5,514,152 A | 5/1996 | Smith |
| 5,525,518 A | 6/1996 | Lundsgaard et al. |
| 5,527,892 A | 6/1996 | Borsotti et al. |
| 5,563,042 A | 10/1996 | Phillips et al. |
| 5,568,806 A | 10/1996 | Cheney, II et al. |
| 5,569,287 A | 10/1996 | Tezuka et al. |
| 5,575,403 A | 11/1996 | Charlton et al. |
| 5,577,499 A | 11/1996 | Teves |
| 5,582,184 A | 12/1996 | Erickson et al. |
| 5,586,553 A | 12/1996 | Halili et al. |
| 5,591,139 A | 1/1997 | Lin et al. |
| 5,593,838 A | 1/1997 | Zanzucchi et al. |
| 5,611,809 A | 3/1997 | Marshall et al. |
| 5,624,458 A | 4/1997 | Lipscher |
| 5,630,986 A | 5/1997 | Charlton et al. |
| 5,632,410 A | 5/1997 | Moulton et al. |
| 5,636,632 A | 6/1997 | Bommannan et al. |
| 5,647,851 A | 7/1997 | Pokras |
| 5,658,515 A | 8/1997 | Lee et al. |
| 5,660,791 A | 8/1997 | Brenneman |
| 5,670,031 A | 9/1997 | Hintsche et al. |
| 5,676,850 A | 10/1997 | Reed et al. |

(56) References Cited

U.S. PATENT DOCUMENTS

| | | |
|---|---|---|
| 5,680,858 A | 10/1997 | Hansen et al. |
| 5,681,484 A | 10/1997 | Zanzucchi et al. |
| 5,682,233 A | 10/1997 | Brinda |
| 5,697,901 A | 12/1997 | Eriksson |
| 5,700,695 A | 12/1997 | Yassinzadeh et al. |
| 5,701,181 A | 12/1997 | Boiarski et al. |
| 5,701,910 A | 12/1997 | Powles et al. |
| D389,761 S | 1/1998 | Thomas |
| 5,705,018 A | 1/1998 | Hartley |
| 5,708,787 A | 1/1998 | Nakano et al. |
| 5,715,417 A | 2/1998 | Gardien et al. |
| 5,730,753 A | 3/1998 | Morita |
| 5,735,273 A | 4/1998 | Kurnik et al. |
| 5,736,103 A | 4/1998 | Pugh |
| 5,741,211 A | 4/1998 | Renirie et al. |
| 5,746,217 A | 5/1998 | Erickson et al. |
| 5,746,720 A | 5/1998 | Stouder, Jr. |
| 5,757,666 A | 5/1998 | Schreiber et al. |
| 5,759,364 A | 6/1998 | Charlton et al. |
| 5,766,066 A | 6/1998 | Ranniger |
| 5,771,890 A | 6/1998 | Tamada |
| 5,797,693 A | 8/1998 | Jaeger |
| 5,800,420 A | 9/1998 | Gross et al. |
| 5,801,057 A | 9/1998 | Smart et al. |
| 5,807,375 A | 9/1998 | Gross et al. |
| 5,820,570 A | 10/1998 | Erickson et al. |
| 5,827,183 A | 10/1998 | Kurnik et al. |
| 5,840,020 A | 11/1998 | Heinonen et al. |
| 5,841,126 A | 11/1998 | Fossum et al. |
| 5,843,692 A | 12/1998 | Phillips et al. |
| 5,846,837 A | 12/1998 | Thym et al. |
| 5,851,215 A | 12/1998 | Mawhirt et al. |
| 5,854,074 A | 12/1998 | Charlton et al. |
| 403,975 A | 1/1999 | Douglas et al. |
| 5,855,801 A | 1/1999 | Lin et al. |
| 5,856,195 A | 1/1999 | Charlton et al. |
| 5,858,194 A | 1/1999 | Bell |
| 5,866,281 A | 2/1999 | Guckel et al. |
| 5,871,494 A | 2/1999 | Simons et al. |
| 5,879,310 A | 3/1999 | Sopp et al. |
| 5,879,326 A | 3/1999 | Godshall et al. |
| 5,879,367 A | 3/1999 | Latterell et al. |
| 5,885,839 A | 3/1999 | Lingane et al. |
| 5,891,053 A | 4/1999 | Sesekura |
| 5,893,870 A | 4/1999 | Talen et al. |
| D411,621 S | 6/1999 | Eisenbarth et al. |
| 5,911,711 A | 6/1999 | Pelkey |
| 5,911,737 A | 6/1999 | Lee et al. |
| 5,912,139 A | 6/1999 | Iwata et al. |
| 5,925,021 A | 7/1999 | Castellano et al. |
| 5,928,207 A | 7/1999 | Pisano et al. |
| 5,930,873 A | 8/1999 | Wyser |
| 5,938,679 A | 8/1999 | Freeman et al. |
| 5,945,678 A | 8/1999 | Yanagisawa |
| 5,951,492 A | 9/1999 | Douglas et al. |
| 5,951,493 A | 9/1999 | Douglas et al. |
| 5,951,521 A | 9/1999 | Mastrototaro et al. |
| 5,954,685 A | 9/1999 | Tierney |
| 5,962,215 A | 10/1999 | Douglas et al. |
| 5,968,760 A | 10/1999 | Phillips et al. |
| 5,968,765 A | 10/1999 | Grage et al. |
| 5,968,836 A | 10/1999 | Matzinger et al. |
| 5,971,941 A | 10/1999 | Simons et al. |
| 5,972,294 A | 10/1999 | Smith et al. |
| 5,986,754 A | 11/1999 | Harding |
| 5,989,409 A | 11/1999 | Kurnik et al. |
| 5,993,189 A | 11/1999 | Mueller et al. |
| D417,504 S | 12/1999 | Love et al. |
| 6,001,067 A | 12/1999 | Shults et al. |
| 6,005,545 A | 12/1999 | Nishida et al. |
| 6,010,463 A | 1/2000 | Lauks et al. |
| 6,010,519 A | 1/2000 | Mawhirt et al. |
| 6,014,135 A | 1/2000 | Fernandes |
| 6,014,577 A | 1/2000 | Henning et al. |
| 6,023,629 A | 2/2000 | Tamada |
| 6,027,459 A | 2/2000 | Shain et al. |
| 6,030,827 A | 2/2000 | Davis et al. |
| 6,032,059 A | 2/2000 | Henning et al. |
| 6,036,924 A | 3/2000 | Simons et al. |
| 6,041,253 A | 3/2000 | Kost et al. |
| 6,045,753 A | 4/2000 | Loewy et al. |
| 6,048,352 A | 4/2000 | Douglas et al. |
| 6,050,988 A | 4/2000 | Zuck |
| 6,056,701 A | 5/2000 | Duchon et al. |
| 6,056,734 A | 5/2000 | Jacobsen et al. |
| 6,058,321 A | 5/2000 | Swayze et al. |
| 6,059,815 A | 5/2000 | Lee et al. |
| 6,061,128 A | 5/2000 | Zweig et al. |
| 6,063,039 A | 5/2000 | Cunningham et al. |
| 6,071,251 A | 6/2000 | Cunningham et al. |
| 6,071,294 A | 6/2000 | Simons et al. |
| 6,077,660 A | 6/2000 | Wong et al. |
| 6,080,116 A | 6/2000 | Erickson et al. |
| 6,083,196 A | 7/2000 | Trautman et al. |
| 6,086,544 A | 7/2000 | Hibner et al. |
| 6,090,790 A | 7/2000 | Eriksson |
| 6,091,975 A | 7/2000 | Daddona et al. |
| 6,093,156 A | 7/2000 | Cunningham et al. |
| 6,097,831 A | 8/2000 | Wieck et al. |
| 6,099,484 A | 8/2000 | Douglas et al. |
| 6,100,107 A | 8/2000 | Lei et al. |
| 6,102,933 A | 8/2000 | Lee et al. |
| 6,103,033 A | 8/2000 | Say et al. |
| 6,103,197 A | 8/2000 | Werner |
| 6,106,751 A | 8/2000 | Talbot et al. |
| 6,118,126 A | 9/2000 | Zanzucchi |
| 6,120,676 A | 9/2000 | Heller et al. |
| 6,123,861 A | 9/2000 | Santini, Jr. et al. |
| 6,126,899 A | 10/2000 | Woudenberg et al. |
| 6,132,449 A | 10/2000 | Lum et al. |
| 6,139,562 A | 10/2000 | Mauze et al. |
| 6,142,939 A | 11/2000 | Eppstein et al. |
| 6,152,942 A | 11/2000 | Brenneman et al. |
| 6,162,639 A | 12/2000 | Douglas |
| 6,172,743 B1 | 1/2001 | Kley et al. |
| 6,175,752 B1 | 1/2001 | Say et al. |
| 6,176,865 B1 | 1/2001 | Mauze et al. |
| 6,183,434 B1 | 2/2001 | Eppstein et al. |
| 6,183,489 B1 | 2/2001 | Douglas et al. |
| 6,187,210 B1 | 2/2001 | Lebouiz et al. |
| 6,192,891 B1 | 2/2001 | Gravel et al. |
| 6,193,873 B1 | 2/2001 | Ohara et al. |
| 6,200,296 B1 | 3/2001 | Dibiasi et al. |
| 6,206,841 B1 | 3/2001 | Cunningham et al. |
| 6,214,626 B1 | 4/2001 | Meller et al. |
| 6,219,574 B1 | 4/2001 | Cormier et al. |
| 6,228,100 B1 | 5/2001 | Schraga |
| 6,230,051 B1 | 5/2001 | Cormier et al. |
| 6,231,531 B1 | 5/2001 | Lum et al. |
| 6,241,862 B1 | 6/2001 | McAleer et al. |
| 6,242,207 B1 | 6/2001 | Douglas et al. |
| 6,245,215 B1 | 6/2001 | Douglas et al. |
| 6,251,083 B1 | 6/2001 | Yum et al. |
| 6,251,260 B1 | 6/2001 | Heller et al. |
| 6,254,586 B1 | 7/2001 | Mann et al. |
| 6,255,061 B1 | 7/2001 | Mori et al. |
| 6,256,533 B1 | 7/2001 | Yuzhakov et al. |
| 6,268,162 B1 | 7/2001 | Phillips et al. |
| 6,271,045 B1 | 8/2001 | Douglas et al. |
| 6,272,364 B1 | 8/2001 | Kurnik |
| 6,283,926 B1 | 9/2001 | Cunningham et al. |
| 6,289,230 B1 | 9/2001 | Chaiken et al. |
| 6,298,254 B2 | 10/2001 | Tamada |
| 6,299,578 B1 | 10/2001 | Kurnik et al. |
| 6,299,757 B1 | 10/2001 | Feldman et al. |
| 6,306,104 B1 | 10/2001 | Cunningham et al. |
| 6,309,351 B1 | 10/2001 | Kurnik et al. |
| D450,711 S | 11/2001 | Istvan et al. |
| 6,312,612 B1 | 11/2001 | Sherman et al. |
| 6,312,812 B1 | 11/2001 | Sherman et al. |
| 6,312,888 B1 | 11/2001 | Wong et al. |
| 6,315,738 B1 | 11/2001 | Nishikawa et al. |
| 6,322,808 B1 | 11/2001 | Trautman et al. |
| 6,329,161 B1 | 12/2001 | Heller et al. |

(56) References Cited

U.S. PATENT DOCUMENTS

| | | |
|---|---|---|
| 6,331,266 B1 | 12/2001 | Powell et al. |
| 6,332,871 B1 | 12/2001 | Douglas et al. |
| 6,334,856 B1 | 1/2002 | Allen et al. |
| 6,350,273 B1 | 2/2002 | Minagawa et al. |
| 6,352,514 B1 | 3/2002 | Douglas et al. |
| 6,356,776 B1 | 3/2002 | Berner et al. |
| 6,358,265 B1 | 3/2002 | Thorne, Jr. et al. |
| 6,364,890 B1 | 4/2002 | Lum et al. |
| 6,375,626 B1 | 4/2002 | Allen et al. |
| 6,375,627 B1 | 4/2002 | Mauze et al. |
| 6,379,969 B1 | 4/2002 | Mauze et al. |
| 6,391,005 B1 | 5/2002 | Lum et al. |
| 6,391,645 B1 | 5/2002 | Huang et al. |
| 6,402,704 B1 | 6/2002 | McMorrow |
| 6,409,679 B2 | 6/2002 | Pyo |
| 6,428,664 B1 | 8/2002 | BhulLar et al. |
| 6,449,608 B1 | 9/2002 | Morita et al. |
| 6,455,324 B1 | 9/2002 | Douglas |
| 6,493,069 B1 | 12/2002 | Nagashimada |
| 6,500,134 B1 | 12/2002 | Cassone |
| 6,520,973 B1 | 2/2003 | McGarry |
| 6,530,892 B1 | 3/2003 | Kelly |
| 6,537,243 B1 | 3/2003 | Henning et al. |
| 6,540,675 B2 | 4/2003 | Aceti et al. |
| 6,544,475 B1 | 4/2003 | Douglas et al. |
| 6,549,796 B2 | 4/2003 | Sohrab |
| 6,555,061 B1 | 4/2003 | Leong et al. |
| 6,558,624 B1 | 5/2003 | Lemmon et al. |
| 6,579,690 B1 | 6/2003 | Bonnecaze et al. |
| 6,589,260 B1 | 7/2003 | Schmelzeisen-Redeker et al. |
| 6,591,125 B1 | 7/2003 | Buse et al. |
| 6,602,205 B1 | 8/2003 | Erickson et al. |
| 6,612,111 B1 | 9/2003 | Hodges et al. |
| 6,616,616 B2 | 9/2003 | Fritz et al. |
| 6,626,874 B1 | 9/2003 | Duchamp |
| 6,656,167 B2 | 12/2003 | Numao et al. |
| 6,679,852 B1 | 1/2004 | Schmelzeisen-Redeker et al. |
| 6,706,000 B2 | 3/2004 | Perez et al. |
| 6,706,049 B2 | 3/2004 | Moerman |
| 6,706,159 B2 | 3/2004 | Moerman et al. |
| 6,740,800 B1 | 5/2004 | Cunningham |
| 6,743,635 B2 | 6/2004 | Neel et al. |
| 6,748,275 B2 | 6/2004 | Lattner et al. |
| 6,753,187 B2 | 6/2004 | Cizdziel et al. |
| 6,766,817 B2 | 7/2004 | da Silva |
| 6,793,633 B2 | 9/2004 | Douglas et al. |
| 6,830,669 B2 | 12/2004 | Miyazaki et al. |
| 6,836,678 B2 | 12/2004 | Tu |
| 6,837,858 B2 | 1/2005 | Cunningham et al. |
| 6,847,451 B2 | 1/2005 | Pugh |
| 6,849,052 B2 | 2/2005 | Uchigaki et al. |
| 6,896,850 B2 | 5/2005 | Subramanian et al. |
| 6,918,404 B2 | 7/2005 | Da Silva |
| 6,919,960 B2 | 7/2005 | Hansen et al. |
| 6,923,764 B2 | 8/2005 | Aceti et al. |
| 6,936,476 B1 | 8/2005 | Anderson et al. |
| 511,214 A1 | 11/2005 | Sasano et al. |
| 6,988,996 B2 | 1/2006 | Roe et al. |
| 7,004,928 B2 | 2/2006 | Aceti et al. |
| 7,011,630 B2 | 3/2006 | Desai et al. |
| 7,025,774 B2 | 4/2006 | Freeman et al. |
| D519,868 S | 5/2006 | Sasano et al. |
| 7,052,652 B2 | 5/2006 | Zanzucchi et al. |
| 7,066,586 B2 | 6/2006 | Da Silva |
| 7,066,890 B1 | 6/2006 | Lam et al. |
| 7,141,058 B2 | 11/2006 | Briggs et al. |
| 7,156,809 B2 | 1/2007 | Quy |
| 7,163,616 B2 | 1/2007 | Vreeke et al. |
| 7,192,061 B2 | 3/2007 | Martin |
| D540,343 S | 4/2007 | Cummins |
| 7,223,365 B2 | 5/2007 | Von Der Goltz |
| 7,225,008 B1 | 5/2007 | Ward et al. |
| 7,226,461 B2 | 6/2007 | Boecker et al. |
| 7,258,673 B2 | 8/2007 | Racchini et al. |
| D551,243 S | 9/2007 | Young |
| 7,270,970 B2 | 9/2007 | Anderson et al. |
| 7,297,151 B2 | 11/2007 | Boecker et al. |
| 7,299,081 B2 | 11/2007 | Mace et al. |
| 7,343,188 B2 | 3/2008 | Sohrab |
| 7,344,507 B2 | 3/2008 | Briggs et al. |
| 7,379,167 B2 | 5/2008 | Mawhirt et al. |
| 7,427,377 B2 | 9/2008 | Zanzucchi et al. |
| D580,068 S | 11/2008 | Shigesada et al. |
| D580,558 S | 11/2008 | Shigesada et al. |
| D599,373 S | 9/2009 | Kobayashi et al. |
| D601,257 S | 9/2009 | Berlinger |
| 7,585,278 B2 | 9/2009 | Aceti et al. |
| D601,444 S | 10/2009 | Jones et al. |
| D601,578 S | 10/2009 | Poulet et al. |
| 7,682,318 B2 | 3/2010 | Alden et al. |
| D622,393 S | 8/2010 | Gatrall et al. |
| 7,780,631 B2 | 8/2010 | Lum et al. |
| 7,803,123 B2 | 9/2010 | Perez et al. |
| 7,879,058 B2 | 2/2011 | Ikeda |
| 7,887,494 B2 | 2/2011 | Emery et al. |
| D642,191 S | 7/2011 | Barnett et al. |
| 7,988,644 B2 | 8/2011 | Freeman et al. |
| 8,012,103 B2 | 9/2011 | Escutia et al. |
| 8,012,104 B2 | 9/2011 | Escutia et al. |
| 8,105,849 B2 * | 1/2012 | McDevitt et al. ............ 436/518 |
| D654,926 S | 2/2012 | Lipman et al. |
| 8,173,439 B2 | 5/2012 | Petrich et al. |
| 8,184,273 B2 | 5/2012 | Dosmann et al. |
| 8,231,832 B2 | 7/2012 | Zanzucchi et al. |
| 8,251,920 B2 | 8/2012 | Vreeke et al. |
| 8,298,255 B2 | 10/2012 | Conway et al. |
| 8,303,518 B2 | 11/2012 | Aceti et al. |
| 8,360,993 B2 | 1/2013 | Escutia et al. |
| 8,360,994 B2 | 1/2013 | Escutia et al. |
| 8,372,015 B2 | 2/2013 | Escutia et al. |
| 8,376,959 B2 | 2/2013 | Deck |
| 8,382,681 B2 | 2/2013 | Escutia et al. |
| 8,391,940 B2 | 3/2013 | Matzinger et al. |
| D691,174 S | 10/2013 | Lipman et al. |
| 8,574,168 B2 | 11/2013 | Freeman et al. |
| 8,702,624 B2 | 4/2014 | Alden |
| 8,795,201 B2 | 8/2014 | Escutia et al. |
| 8,801,631 B2 | 8/2014 | Escutia et al. |
| 8,919,605 B2 | 12/2014 | Lipman et al. |
| 8,969,097 B2 | 3/2015 | Emery et al. |
| 9,060,723 B2 | 6/2015 | Escutia et al. |
| 9,060,727 B2 | 6/2015 | Saikley et al. |
| 9,095,292 B2 | 8/2015 | Zanzucchi et al. |
| 9,149,215 B2 | 10/2015 | Werner et al. |
| 9,366,636 B2 | 6/2016 | Emery et al. |
| 9,380,974 B2 | 7/2016 | Litherland et al. |
| 2001/0001034 A1 | 5/2001 | Douglas |
| 2001/0027277 A1 | 10/2001 | Klitmose |
| 2001/0027328 A1 | 10/2001 | Lum et al. |
| 2001/0053891 A1 | 12/2001 | Ackley |
| 2002/0002326 A1 | 1/2002 | Causey, III et al. |
| 2002/0002344 A1 | 1/2002 | Douglas et al. |
| 2002/0004640 A1 | 1/2002 | Conn et al. |
| 2002/0006355 A1 | 1/2002 | Whitson |
| 2002/0016568 A1 | 2/2002 | Lebel et al. |
| 2002/0020688 A1 | 2/2002 | Sherman et al. |
| 2002/0022934 A1 | 2/2002 | Vogel et al. |
| 2002/0023852 A1 | 2/2002 | Mcivor et al. |
| 2002/0042594 A1 | 4/2002 | Lum et al. |
| 2002/0052618 A1 | 5/2002 | Haar et al. |
| 2002/0087056 A1 | 7/2002 | Aceti et al. |
| 2002/0136667 A1 | 9/2002 | Subramanian et al. |
| 2002/0137998 A1 | 9/2002 | Smart et al. |
| 2002/0160520 A1 | 10/2002 | Orloff et al. |
| 2002/0168290 A1 | 11/2002 | Yuzhakov et al. |
| 2002/0169394 A1 | 11/2002 | Eppstein et al. |
| 2002/0169411 A1 | 11/2002 | Sherman et al. |
| 2002/0177761 A1 | 11/2002 | Orloff et al. |
| 2002/0177764 A1 | 11/2002 | Sohrab |
| 2002/0183102 A1 | 12/2002 | Withers et al. |
| 2002/0188223 A1 | 12/2002 | Perez et al. |
| 2002/0198444 A1 | 12/2002 | Uchigaki et al. |
| 2003/0012693 A1 | 1/2003 | Otillar et al. |
| 2003/0028087 A1 | 2/2003 | Yuzhakov et al. |

(56) References Cited

U.S. PATENT DOCUMENTS

| | | |
|---|---|---|
| 2003/0028125 A1 | 2/2003 | Yuzhakov et al. |
| 2003/0039587 A1 | 2/2003 | Niermann |
| 2003/0083685 A1 | 5/2003 | Freeman et al. |
| 2003/0083686 A1 | 5/2003 | Freeman et al. |
| 2003/0105961 A1 | 6/2003 | Zatloukal et al. |
| 2003/0116596 A1 | 6/2003 | Terasawa |
| 2003/0135166 A1 | 7/2003 | Gonnelli |
| 2003/0135333 A1 | 7/2003 | Aceti |
| 2003/0143746 A1 | 7/2003 | Sage |
| 2003/0153844 A1 | 8/2003 | Smith et al. |
| 2003/0153900 A1 | 8/2003 | Aceti et al. |
| 2003/0175987 A1 | 9/2003 | Verdonk et al. |
| 2003/0206302 A1 | 11/2003 | Pugh |
| 2003/0207441 A1 | 11/2003 | Eyster et al. |
| 2003/0208113 A1 | 11/2003 | Mault et al. |
| 2003/0211619 A1 | 11/2003 | Olson et al. |
| 2003/0212344 A1 | 11/2003 | Yuzhakov et al. |
| 2003/0212347 A1 | 11/2003 | Sohrab |
| 2003/0216628 A1 | 11/2003 | Bortz et al. |
| 2004/0010207 A1 | 1/2004 | Flaherty et al. |
| 2004/0030353 A1 | 2/2004 | Schmelzeisen-redeker et al. |
| 2004/0039303 A1 | 2/2004 | Wurster et al. |
| 2004/0049219 A1 | 3/2004 | Briggs et al. |
| 2004/0059256 A1 | 3/2004 | Perez |
| 2004/0072357 A1 | 4/2004 | Stiene et al. |
| 2004/0073140 A1 | 4/2004 | Douglas |
| 2004/0092842 A1 | 5/2004 | Boecker et al. |
| 2004/0092995 A1 | 5/2004 | Boecker et al. |
| 2004/0094432 A1 | 5/2004 | Neel et al. |
| 2004/0096959 A1 | 5/2004 | Stiene et al. |
| 2004/0097796 A1 | 5/2004 | Berman et al. |
| 2004/0098009 A1 | 5/2004 | Boecker et al. |
| 2004/0102803 A1 | 5/2004 | Boecker et al. |
| 2004/0122339 A1 | 6/2004 | Roe et al. |
| 2004/0132167 A1 | 7/2004 | Rule et al. |
| 2004/0138588 A1 | 7/2004 | Saikley et al. |
| 2004/0155084 A1 | 8/2004 | Brown |
| 2004/0157339 A1 | 8/2004 | Burke et al. |
| 2004/0178218 A1 | 9/2004 | Schomakers et al. |
| 2004/0186394 A1 | 9/2004 | Roe et al. |
| 2004/0191119 A1 | 9/2004 | Zanzucchi et al. |
| 2004/0202576 A1 | 10/2004 | Aceti et al. |
| 2004/0230216 A1 | 11/2004 | LeVaughn et al. |
| 2004/0236251 A1 | 11/2004 | Roe et al. |
| 2004/0238675 A1 | 12/2004 | Banaszkiewicz et al. |
| 2004/0242982 A1 | 12/2004 | Sakata et al. |
| 2004/0249253 A1 | 12/2004 | Racchini et al. |
| 2004/0259180 A1 | 12/2004 | Burke et al. |
| 2005/0004494 A1 | 1/2005 | Perez et al. |
| 2005/0010134 A1 | 1/2005 | Douglas et al. |
| 2005/0015020 A1 | 1/2005 | LeVaughn et al. |
| 2005/0027182 A1 | 2/2005 | Siddiqui et al. |
| 2005/0038680 A1 | 2/2005 | McMahon |
| 2005/0070819 A1 | 3/2005 | Poux et al. |
| 2005/0096686 A1 | 5/2005 | Allen |
| 2005/0106713 A1 | 5/2005 | Phan et al. |
| 2005/0109386 A1 | 5/2005 | Marshall |
| 2005/0159678 A1 | 7/2005 | Taniike et al. |
| 2005/0187532 A1 | 8/2005 | Thurau et al. |
| 2005/0192492 A1 | 9/2005 | Cho et al. |
| 2005/0202567 A1 | 9/2005 | Zanzucchi et al. |
| 2005/0202733 A1 | 9/2005 | Yoshimura et al. |
| 2005/0209518 A1 | 9/2005 | Sage, Jr. et al. |
| 2005/0215872 A1 | 9/2005 | Berner et al. |
| 2005/0215923 A1 | 9/2005 | Wiegel |
| 2005/0245844 A1 | 11/2005 | Mace et al. |
| 2005/0255001 A1 | 11/2005 | Padmaabhan et al. |
| 2005/0277972 A1 | 12/2005 | Wong et al. |
| 2006/0008389 A1 | 1/2006 | Sacherer et al. |
| 2006/0036134 A1 | 2/2006 | Tarassenko et al. |
| 2006/0052724 A1 | 3/2006 | Roe |
| 2006/0064035 A1 | 3/2006 | Wang et al. |
| 2006/0094985 A1 | 5/2006 | Aceti et al. |
| 2006/0117616 A1 | 6/2006 | Jones et al. |
| 2006/0122536 A1 | 6/2006 | Haar et al. |
| 2006/0135873 A1 | 6/2006 | Karo et al. |
| 2006/0155317 A1 | 7/2006 | List |
| 2006/0161078 A1 | 7/2006 | Schraga |
| 2006/0178600 A1 | 8/2006 | Kennedy et al. |
| 2006/0189908 A1 | 8/2006 | Kennedy |
| 2006/0204399 A1 | 9/2006 | Freeman et al. |
| 2006/0229533 A1 | 10/2006 | Hoenes et al. |
| 2006/0241517 A1 | 10/2006 | Fowler et al. |
| 2006/0257993 A1 | 11/2006 | Mcdevitt et al. |
| 2006/0259102 A1 | 11/2006 | Slatkine |
| 2006/0281187 A1 | 12/2006 | Emery et al. |
| 2007/0016104 A1 | 1/2007 | Jansen et al. |
| 2007/0017824 A1 | 1/2007 | Rippeth et al. |
| 2007/0033074 A1 | 2/2007 | Nitzan et al. |
| 2007/0060842 A1 | 3/2007 | Alvarez-Icaza et al. |
| 2007/0078313 A1 | 4/2007 | Emery et al. |
| 2007/0078358 A1 | 4/2007 | Escutia et al. |
| 2007/0083130 A1 | 4/2007 | Thomson et al. |
| 2007/0083131 A1 | 4/2007 | Escutia et al. |
| 2007/0093786 A1 | 4/2007 | Goldsmith et al. |
| 2007/0112281 A1 | 5/2007 | Olson |
| 2007/0179404 A1 | 8/2007 | Escutia et al. |
| 2007/0179405 A1 | 8/2007 | Emery et al. |
| 2007/0253531 A1* | 11/2007 | Okuzawa et al. ............. 378/62 |
| 2007/0255181 A1 | 11/2007 | Alvarez-Icaza et al. |
| 2007/0255302 A1 | 11/2007 | Koeppel et al. |
| 2008/0012701 A1 | 1/2008 | Kass et al. |
| 2008/0046831 A1 | 2/2008 | Imai et al. |
| 2008/0077048 A1 | 3/2008 | Escutia et al. |
| 2008/0139910 A1* | 6/2008 | Mastrototaro ...... G06F 19/3456 600/365 |
| 2008/0194934 A1 | 8/2008 | Ray et al. |
| 2008/0268485 A1 | 10/2008 | Guarino et al. |
| 2008/0269625 A1 | 10/2008 | Halperin et al. |
| 2009/0054810 A1 | 2/2009 | Zanzucchi et al. |
| 2009/0149717 A1 | 6/2009 | Brauer et al. |
| 2009/0156923 A1* | 6/2009 | Power et al. ................. 600/365 |
| 2009/0292489 A1 | 11/2009 | Burke et al. |
| 2009/0301899 A1 | 12/2009 | Hodges et al. |
| 2010/0010374 A1 | 1/2010 | Escutia et al. |
| 2010/0021947 A1 | 1/2010 | Emery et al. |
| 2010/0021948 A1* | 1/2010 | Lipman et al. ................. 435/14 |
| 2010/0095229 A1 | 4/2010 | Dixon et al. |
| 2010/0174211 A1 | 7/2010 | Frey et al. |
| 2010/0185120 A1 | 7/2010 | Sacherer et al. |
| 2010/0217155 A1 | 8/2010 | Poux et al. |
| 2010/0331650 A1* | 12/2010 | Batman et al. ............... 600/365 |
| 2011/0098599 A1 | 4/2011 | Emery et al. |
| 2011/0105872 A1 | 5/2011 | Chickering et al. |
| 2011/0201909 A1 | 8/2011 | Emery et al. |
| 2011/0294152 A1 | 12/2011 | Lipman et al. |
| 2012/0296179 A1 | 11/2012 | Zanzucchi et al. |
| 2013/0110516 A1 | 5/2013 | Abulhaj et al. |
| 2013/0158430 A1 | 6/2013 | Aceti et al. |
| 2013/0158432 A1 | 6/2013 | Escutia et al. |
| 2013/0172698 A1 | 7/2013 | Reynolds et al. |
| 2013/0274568 A1 | 10/2013 | Escutia et al. |
| 2013/0274579 A1 | 10/2013 | Richter et al. |
| 2014/0012116 A1 | 1/2014 | Okuyama |
| 2014/0316301 A1 | 10/2014 | Escutia et al. |
| 2014/0336480 A1 | 11/2014 | Escutia et al. |
| 2014/0376762 A1 | 12/2014 | Lipman et al. |
| 2015/0037898 A1 | 2/2015 | Baldus et al. |
| 2015/0153351 A1 | 6/2015 | Lipman et al. |
| 2015/0212006 A1 | 7/2015 | Emery et al. |
| 2016/0038066 A1 | 2/2016 | Escutia et al. |

FOREIGN PATENT DOCUMENTS

| | | |
|---|---|---|
| DE | 197 05 091 A1 | 2/1999 |
| DE | 199 22 413 A1 | 11/2000 |
| DE | 103 02-501 A1 | 8/2004 |
| EP | 0 103 426 A2 | 3/1984 |
| EP | 0 256 806 A2 | 2/1988 |
| EP | 0 396-016 A2 | 11/1990 |
| EP | 0 396-016 A3 | 11/1990 |
| EP | 0 397 424 A2 | 11/1990 |
| EP | 0 762 311 A2 | 3/1997 |
| EP | 0 255-338 A2 | 2/1998 |

(56) References Cited

FOREIGN PATENT DOCUMENTS

| | | | |
|---|---|---|---|
| EP | 0 849 584 A2 | 6/1998 | |
| EP | 1 266-607 A2 | 12/2002 | |
| EP | 1 266-607 A3 | 12/2002 | |
| EP | 1369688 * | 10/2003 | ............. G01N 33/49 |
| EP | 1 360-934 A1 | 11/2003 | |
| EP | 1 360-934 B1 | 11/2003 | |
| EP | 1 486-766 A1 | 12/2004 | |
| EP | 1 486-766 B1 | 12/2004 | |
| EP | 1 529-489 A1 | 5/2005 | |
| EP | 1 529-489 B1 | 5/2005 | |
| EP | 1 769-735 A1 | 4/2007 | |
| EP | 1 987 766 A2 | 11/2008 | |
| JP | 63-305841 A | 12/1988 | |
| JP | 3-63570 A | 3/1991 | |
| JP | 03093189 A | 4/1991 | |
| JP | 7-67861 A | 3/1995 | |
| JP | 7-213925 A | 8/1995 | |
| JP | 9-168530 A | 6/1997 | |
| JP | 9-313465 A | 9/1997 | |
| JP | 9-266889 A | 10/1997 | |
| JP | 9-294737 A | 11/1997 | |
| JP | 10-024028 A | 1/1998 | |
| JP | 10-505258 A | 5/1998 | |
| JP | 10-508518 A | 8/1998 | |
| JP | 10-318970 A | 12/1998 | |
| JP | 11056822 A | 3/1999 | |
| JP | 11281779 A | 10/1999 | |
| JP | 2000-116629 A | 4/2000 | |
| JP | 2000-126161 A | 5/2000 | |
| JP | 2000-168754 A | 6/2000 | |
| JP | 2000-254111 A | 9/2000 | |
| JP | 2001-159618 A | 6/2001 | |
| JP | 2001-515203 A | 9/2001 | |
| JP | 2001-305096 A | 10/2001 | |
| JP | 2001-330581 A | 11/2001 | |
| JP | 2002-502045 A | 1/2002 | |
| JP | 2002-085384 A | 3/2002 | |
| JP | 2002-514453 A | 5/2002 | |
| JP | 2002-168862 A | 6/2002 | |
| JP | 2003-507719 A | 2/2003 | |
| JP | 2003-108679 A | 4/2003 | |
| JP | 2003-180417 A2 | 7/2003 | |
| JP | 2004-000598 A | 1/2004 | |
| JP | 2004-500948 A | 1/2004 | |
| JP | 2004-117339 A | 4/2004 | |
| JP | 2004-202256 A | 7/2004 | |
| JP | 2004-209266 A | 7/2004 | |
| JP | 2004-519302 A | 7/2004 | |
| JP | 2004-522500 A | 7/2004 | |
| JP | 2004-528936 A | 9/2004 | |
| JP | 2005-503538 A | 2/2005 | |
| JP | 2005-087613 A | 4/2005 | |
| JP | 2006-512969 A | 4/2005 | |
| JP | 3638958 B2 | 4/2005 | |
| JP | 2005-525149 A | 8/2005 | |
| JP | 2005-237938 A | 9/2005 | |
| JP | 2005-525846 A | 9/2005 | |
| JP | 2005-527254 A | 9/2005 | |
| JP | 2006-506185 A | 2/2006 | |
| JP | 2006-512974 A | 4/2006 | |
| JP | 2006-516723 A | 7/2006 | |
| JP | 2006-521555 A | 9/2006 | |
| JP | 2006-527013 A | 11/2006 | |
| JP | 2007-054407 A | 3/2007 | |
| JP | 2007-067698 A | 3/2007 | |
| JP | 2007-521031 A | 8/2007 | |
| JP | 2007-311196 A | 11/2007 | |
| JP | 2007-537804 A | 12/2007 | |
| JP | 2008-125813 A | 6/2008 | |
| WO | WO-86/05966 A1 | 10/1986 | |
| WO | WO-88/00812 A1 | 2/1988 | |
| WO | WO-88/07666 A1 | 10/1988 | |
| WO | WO-91/14212 A1 | 9/1991 | |
| WO | WO-94/13203 A1 | 6/1994 | |
| WO | WO-95/10223 A2 | 4/1995 | |
| WO | WO-95/10223 A3 | 4/1995 | |
| WO | WO-96/04857 A1 | 2/1996 | |
| WO | WO-96/07907 A1 | 3/1996 | |
| WO | WO-96/14026 A1 | 5/1996 | |
| WO | WO-96/25088 A1 | 8/1996 | |
| WO | WO-97/15227 A1 | 5/1997 | |
| WO | WO-97/29847 A1 | 8/1997 | |
| WO | WO-97/30344 A1 | 8/1997 | |
| WO | WO-97/41421 A1 | 11/1997 | |
| WO | WO-97/42885 A1 | 11/1997 | |
| WO | WO-97/42888 A1 | 11/1997 | |
| WO | WO-97/43962 A1 | 11/1997 | |
| WO | WO-98/00193 A1 | 1/1998 | |
| WO | WO-98/31275 A1 | 7/1998 | |
| WO | WO-98/35225 A1 | 8/1998 | |
| WO | WO-99/12008 A1 | 3/1999 | |
| WO | WO-99/23492 A1 | 5/1999 | |
| WO | WO-99/44508 A1 | 9/1999 | |
| WO | WO-99/56954 A1 | 11/1999 | |
| WO | WO-99/58051 A1 | 11/1999 | |
| WO | WO-99/62576 A1 | 12/1999 | |
| WO | WO-00/09184 A1 | 2/2000 | |
| WO | WO-00/13573 A1 | 3/2000 | |
| WO | WO-00/14269 A1 | 3/2000 | |
| WO | WO-00/14535 A1 | 3/2000 | |
| WO | WO-00/18449 A2 | 4/2000 | |
| WO | WO-00/18449 A3 | 4/2000 | |
| WO | WO-00/36400 A1 | 6/2000 | |
| WO | WO-00/42422 A1 | 7/2000 | |
| WO | WO-00/74763 A2 | 12/2000 | |
| WO | WO-00/74763 A3 | 12/2000 | |
| WO | WO-00/78208 A1 | 12/2000 | |
| WO | WO-01/13795 A1 | 3/2001 | |
| WO | WO-01/16575 A1 | 3/2001 | |
| WO | WO-01/52727 A1 | 7/2001 | |
| WO | WO-01/64105 A1 | 9/2001 | |
| WO | WO-01/64105 C2 | 9/2001 | |
| WO | WO-01/72220 A1 | 10/2001 | |
| WO | WO-01/80728 A1 | 11/2001 | |
| WO | WO-01/85233 A2 | 11/2001 | |
| WO | WO-01/85233 A3 | 11/2001 | |
| WO | WO-01/91634 A2 | 12/2001 | |
| WO | WO-01/91634 A3 | 12/2001 | |
| WO | WO-02/00101 A2 | 1/2002 | |
| WO | WO-02/00101 A3 | 1/2002 | |
| WO | WO-02/49507 A1 | 6/2002 | |
| WO | WO-02/49509 A2 | 6/2002 | |
| WO | WO-02/49509 A3 | 6/2002 | |
| WO | WO-02/078533 A2 | 10/2002 | |
| WO | WO-02/078533 A3 | 10/2002 | |
| WO | WO-02/082052 A2 | 10/2002 | |
| WO | WO-02/082052 A3 | 10/2002 | |
| WO | WO-02/093144 A1 | 11/2002 | |
| WO | WO-02/100251 A2 | 12/2002 | |
| WO | WO-02/100251 A3 | 12/2002 | |
| WO | WO-02/101359 A2 | 12/2002 | |
| WO | WO-02/101359 A3 | 12/2002 | |
| WO | WO-03/007819 A1 | 1/2003 | |
| WO | WO-2003/030984 A1 | 4/2003 | |
| WO | WO-2003/066128 A2 | 8/2003 | |
| WO | WO-2003/066128 A3 | 8/2003 | |
| WO | WO-2003/070099 A1 | 8/2003 | |
| WO | WO-2003/071940 A1 | 9/2003 | |
| WO | WO-2003/071940 C1 | 9/2003 | |
| WO | WO-2004/045375 A2 | 6/2004 | |
| WO | WO-2004/045375 A3 | 6/2004 | |
| WO | WO-2004/062499 A1 | 7/2004 | |
| WO | WO-2004/062500 A1 | 7/2004 | |
| WO | WO-2004/062500 C1 | 7/2004 | |
| WO | WO-2004/064636 A1 | 8/2004 | |
| WO | WO-2004/085995 A2 | 10/2004 | |
| WO | WO-2004/085995 A3 | 10/2004 | |
| WO | WO-2004/091693 A2 | 10/2004 | |
| WO | WO-2004/091693 A3 | 10/2004 | |
| WO | WO-2004/105827 A2 | 12/2004 | |
| WO | WO-2004/105827 A3 | 12/2004 | |
| WO | WO-2005/006939 A2 | 1/2005 | |
| WO | WO-2005/006939 A3 | 1/2005 | |
| WO | WO-2005/009238 A1 | 2/2005 | |

(56) References Cited

FOREIGN PATENT DOCUMENTS

| | | |
|---|---|---|
| WO | WO-2005/013824 A1 | 2/2005 |
| WO | WO-2005/018709 A2 | 3/2005 |
| WO | WO-2005/018709 A3 | 3/2005 |
| WO | WO-2005/018710 A2 | 3/2005 |
| WO | WO-2005/018710 A3 | 3/2005 |
| WO | WO-2005/084543 A1 | 9/2005 |
| WO | WO-2005/084546 A2 | 9/2005 |
| WO | WO-2005/084546 A3 | 9/2005 |
| WO | WO-2005/085995 A1 | 9/2005 |
| WO | WO-2005/112763 A1 | 12/2005 |
| WO | WO-2006/138226 A2 | 12/2006 |
| WO | WO-2006/138226 A3 | 12/2006 |
| WO | WO-2007/041062 A2 | 4/2007 |
| WO | WO-2007/041062 A3 | 4/2007 |
| WO | WO-2007/041063 A2 | 4/2007 |
| WO | WO-2007/041063 A3 | 4/2007 |
| WO | WO-2007/041244 A2 | 4/2007 |
| WO | WO-2007/041244 A3 | 4/2007 |
| WO | WO-2007/041287 A2 | 4/2007 |
| WO | WO-2007/041287 A3 | 4/2007 |
| WO | WO-2007/041355 A2 | 4/2007 |
| WO | WO-2007/041355 A3 | 4/2007 |
| WO | WO-2007/108519 A1 | 9/2007 |
| WO | WO-2007/112034 A2 | 10/2007 |
| WO | WO-2007/112034 A3 | 10/2007 |
| WO | WO-2007/131036 A1 | 11/2007 |
| WO | WO-2008/027319 A2 | 3/2008 |
| WO | WO-2008/027319 A3 | 3/2008 |
| WO | WO-2008/062648 A1 | 5/2008 |
| WO | WO-2009/145920 A1 | 12/2009 |
| WO | WO-2009/148624 A1 | 12/2009 |
| WO | WO-2009/148626 A1 | 12/2009 |
| WO | WO-2011/065981 A1 | 6/2011 |
| WO | WO-2011/162823 A1 | 12/2011 |
| WO | WO-2012/127870 A1 | 9/2012 |
| WO | WO-2013/020103 A1 | 2/2013 |
| WO | WO-2014/205412 A1 | 12/2014 |

OTHER PUBLICATIONS

ADA (Jan. 1994). "Self-Monitoring of Blood Glucose," Consensus Statement *Diabetes Care* 17(1):81-86.

Anonymous. (Sep. 30, 1993). "The Effect of Intensive Treatment of Diabetes on the Development and Progression of Long-Term Complications in Insulin-Dependent Diabetes Mellitus." *The New England Journal of Medicine* 329(14):977-986.

Anonymous. (Jun. 23, 1998). Taking the "Ouch" Out of Needles: Arrays of "Microneedles" Offer New Techniques for Drug Delivery, *Science Daily*, located at <http:www.sciencedaily.com/releases/1998/06/980623045850.htm>, last visited Jan. 14, 2014, 3 pages.

Beregszàszi, M. et al. (Jul. 1997). "Nocturnal Hypoglycemia in Children and Adolescents with Insulin-Dependent Diabetes Mellitus: Prevalence and Risk Factors," *J. Pediatrics* 131(1 Pt. 1):27-33.

Chase, H.P. et al. (Feb. 2001). "Continuous Subcutaneous Glucose Monitoring in Children with Type 1 Diabetes," *Pediatrics* 107(2):222-226.

Clarke, W.L. et al. (Sep.-Oct. 1987). "Evaluating Clinical Accuracy of Systems for Self-Monitoring of Blood Glucose," *Diabetes Care* 10(5):622-628.

Collison, M.E. et al. (Sep. 1999). "Analytical Characterization of Electrochemical Biosensor Test Strips for Measurement of Glucose in Low-Volume Interstitial Fluid Samples," *Clinical Chemistry* 45(9):1665-1673.

Coster, S. et al. (2000). "Monitoring Blood Glucose Control in Diabetes Mellitus: a Systematic Review." *Health Technology Assessment* 4(12):1-93.

Cox, D.J. et al. (Jun. 1997). "Understanding Error Grid Analysis," *Diabetes Care* 20(6):911-912.

D'Arrigo, T.D. (Mar. 2000). "GlucoWatch Monitor Poised for Approval," *Diabetes Forecast*, 53(3):43-44.

Feldman, B. et al. (2000). "FreeStyle™: A Small-Volume Electrochemical Glucose Sensor for Home Blood Glucose Testing," *Diabetes Technology and Therapeutics*, 2(2):221-229.

Johnson, R.N. et al. (Jan. 1998). "Accuracy of Devices Used for Self-Monitoring of Blood Glucose," *Annals of Clinical Biochemistry* 35(1):68-74.

Johnson, R.N. et al. (Jan. 1999). "Analytical Error of Home Glucose Monitors: A Comparison of 18 Systems," *Annals of Clinical Biochemistry* 36(1):72-79.

Johnson, R.N. et al. (2001). "Error Detection and Measurement in Glucose Monitors," *Clinica Chimica Acta* 307:61-67.

Kumetrix, Inc. (Dec. 1999). "Painless Blood Glucose Monitoring, Courtesy of the Mosquito," *Start-Up* pp. 27-28.

Lee, S-C. (Jun. 1999). "Light Scattering by Closely Spaced Parallel Cylinders Embedded in a Finite Dielectric Slab," *Journal of the Optical Society of America A* 16(6):1350-1361.

McGarraugh, G. et al. (2001). "Physiological Influences on Off-Finger Glucose Testing," *Diabetes Technology & Therapeutics* 3(3):367-376.

McNichols, R.J. et al. (Jan. 2000). "Optical Glucose Sensing in Biological Fluids: An Overview," *Journal of Biomedical Optics*, 5(1):5-16.

Mahler, R.J. et al. (1999). "Clinical Review 102, Type 2 Diabetes Melitus: Update on Diagnosis Pathophysiology, and Treatment," *The Journal of Clinical Endocrinology and Metabolism* 84(4):1165-1171.

Medline Plus. (Jun. 17, 2008)., Medical Encyclopedia, Monitor Blood Glucose-Series: Part 1-4, 6 pages.

Neeley, W.E. et al. (1981). "An Instrument for Digital Matrix Photometry," *Clinical Chemistry* 27(10):1665-1668.

Neeley, W.E. (1983). "Reflectance Digital Matrix Photometry," *Clinical Chemistry* 29(6):1038-1041.

Neeley, W.E. (1983). "Multilayer Film Analysis for Glucose in 1-µL Samples of Plasma," *Clinical Chemistry* 29(12):2103-2105.

Neeley, W.E. (1988). "A Reflectance Photometer with a Square Photodiode Array Detector for Use on Multilayer Dry-Film Slides," *Clinical Chemistry* 34(11):2367-2370.

Otto, E. et al. (2000). "An Intelligent Diabetes Software Prototype: Predicting Blood Glucose Levels and Recommending Regimen Changes," *Diabetes Technology and Therapeutics* 2(4):569-576.

Pfohl, M. et al. (2000). "Spot Glucose Measurement in Epidermal Interstitial Fluid—An Alternative to Capillary Blood Glucose Estimation," *Experimental and Clinical Endocrinology & Diabetes* 108(1):1-4.

Princen, H.M. (May 1969). "Capillary Phenomena in Assemblies of Parallel Cylinders, I. Capillary Rise Between Two Cylinders," *Journal of Colloid and Interface Science* 30(1):69-75.

Princen, H.M. (Jul. 1969). "Capillary Phenomena in Assemblies of Parallel Cylinders, II. Capillary Rise in Systems with More Than Two Cylinders," *Journal of Colloid and Interface Science* 30(3):359-371.

Rebrin, K. et al. (Sep. 1999). "Subcutaneous Glucose Predicts Plasma Glucose Independent of Insulin: Implications for Continuous Monitoring," *American Journal of Physiology* 277(3):E561-E571.

Rosen, S. (1999). "Road to New-Age Glucose Monitoring Still Rocky," *Diagnostic Insight*, pp. 4-5, 12-13, 16.

Smart, W.H. et al. (2000). "The Use of Silicon Microfabrication Technology in Painless Glucose Monitoring," *Diabetes Technology & Therapeutics* 2(4):549-559.

Svedman, C. et al. (Apr. 1999). "Skin Mini-Erosion Technique for Monitoring Metabolites in Interstitial Fluid: Its Feasibility Demonstrated by OGTT Results in Diabetic and Non-Diabetic Subjects," *Scand. J. Clin. Lab. Invest.* 59(2):115-123.

Trinder, P. (1969). "Determination of Glucose in Blood Using Glucose Oxidase with an Alternate Oxygen Acceptor," *Annals of Clinical Biochemistry* 6:24-28.

Yum, S. I. et al. (Nov. 1, 1999). "Capillary Blood Sampling for Self-Monitoring of Blood Glucose," *Diabetes Technology & Therapeutics*, 1(1):29-37.

Final Office Action dated Mar. 27, 2014, for U.S. Appl. No. 12/457,332, filed Jun. 8, 2009, 10 pages.

(56) References Cited

OTHER PUBLICATIONS

International Search Report dated Jul. 28, 2009, for PCT Application No. PCT/US2009/003445, filed on Jun. 8, 2009, 2 pages.
International Search Report dated Nov. 14, 2011, for PCT Application No. PCT/US2011/001132, filed on Jun. 24, 2011, 2 pages.
Non-Final Office Action dated Mar. 2, 2012, for U.S. Appl. No. 12/457,332, filed Jun. 8, 2009, 7 pages.
Non-Final Office Action dated May 30, 2013, for U.S. Appl. No. 12/457,332, filed Jun. 8, 2009, 9 pages.
Written Opinion dated on Jul. 28, 2009, for PCT Application No. PCT/US2009/003445, filed on Jun. 8, 2009, 4 pages.
Written Opinion dated Nov. 14, 2011, for PCT Application No. PCT/US2011/001132, filed on Jun. 24, 2011, 6 pages.
Brazzle, J. et al. Active Microneedles with Integrated Functionality, Solid-State Sensor and Actuator Workshop, Hilton Head Island, South Carolina, Jun. 4-8, 2000, Technical Digest, 199-202.
Burge, M.R., (Aug. 2001). "Lack of Compliance with Home Blood Glucose Monitoring Predicts Hospitalization in Diabetes", Diabetes Care 24(8): 1502-1503.
Clarke, W.L. et al. (1981). "Evaluation of a New Reflectance Photometer for Use in Home Blood Glucose Monitoring," *Diabetes Care* 4(5):547-550.
Extended European Search Report dated Apr. 19, 2011, for EP Application No. 10 18 0848.3 filed Sep. 28, 2010, 5 pages.
Extended European Search Report dated Feb. 22, 2012, for EP Application No. EP 10 18 1155, filed Sep. 28, 2010, 6 pages.
Extended European Search Report dated Jan. 22, 2013, for EP Application No. 12182900.6, filed on Sep. 29, 2006, 6 pages.
Extended European Search Report dated Apr. 29, 2013 for EP Patent Application No. 12192620.8, filed on Nov. 14, 2012, 8 pages.
Extended European Search Report dated Nov. 8, 2016, for EP Application No. 16 167 087.2, filed on Aug. 3, 2012, 6 pages.
Extended European Search Report dated Jun. 16, 2014, for EP Application No. 09758787.7, filed on Jun. 8, 2009, 6 pages.
Extended European Search Report dated Jul. 18, 2013, for EP Application No. 06 772 943.4, filed on Jun. 13, 2006, 7 pages.
Extended European Search Report dated Aug. 27, 2012, for EP Application No. 09 758 789.3, filed on Jun. 8, 2009, 13 pages.
Extended European Search Report dated Oct. 27, 2016, for EP Application No. 11 798 518.4, filed on Jun. 24, 2011, 7 pages.
Extended European Search Report dated Jan. 20, 2017, for EP Application No. 14 813 126.1, filed Jun. 20, 2014, 8 pages.
Final Office Action dated Jul. 9, 2008, for U.S. Appl. No. 11/529,613, filed Sep. 29, 2006, 19 pages.
Final Office Action dated Nov. 23, 2009, for U.S. Appl. No. 11/529,613, filed Sep. 29, 2006, 20 pages.
Final Office Action dated Jan. 21, 2011, for U.S. Appl. No. 11/529,613, filed Sep. 29, 2006, 7 pages.
Final Office Action dated Aug. 15, 2013 for U.S. Appl. No. 13/562,129, filed Jul. 30, 2012, 12 pages.
Final Office Action dated Apr. 13, 2016, for U.S. Appl. No. 13/669,366, filed Nov. 5, 2012, 31 pages.
Final Office Action dated Aug. 28, 2014, for U.S. Appl. No. 13/562,129, filed Jul. 30, 2012, 11 pages.
Final Office Action dated Dec. 26, 2014, for U.S. Appl. No. 13/669,366, filed Nov. 5, 2012, 9 pages.
Final Office Action dated Jan. 22, 2014, for U.S. Appl. No. 13/669,366, filed Nov. 5, 2012, 8 pages.
Final Office Action dated Jun. 30, 2010, for U.S. Appl. No. 11/529,612, filed Sep. 29, 2006, 11 pages.
Final Office Action dated May 30, 2007, for U.S. Appl. No. 11/125,107, filed May 10, 2005, 11 pages.
Final Office Action dated Nov. 1, 2010, for U.S. Appl. No. 11/311,667, filed Dec. 20, 2005, 9 pages.
Final Office Action dated Nov. 21, 2011, for U.S. Appl. No. 11/311,667, filed Dec. 20, 2005, 8 pages.
Final Office Action dated Jun. 11, 2010, for U.S. Appl. No. 11/529,614, filed Sep. 29, 2006, 16 pages.
Final Office Action dated Mar. 10, 2015, for U.S. Appl. No. 11/529,614, filed Sep. 29, 2006, 24 pages.
Final Office Action dated May 8, 2012, for U.S. Appl. No. 12/457,331, filed Jun. 8, 2009, 7 pages.
Final Office Action dated Dec. 26, 2014, for U.S. Appl. No. 12/457,331, filed Jun. 8, 2009, 9 pages.
Final Office Action dated May 5, 2016, for U.S. Appl. No. 14/311,114, filed Jun. 20, 2014, 13 pages.
Final Office Action dated May 5, 2016, for U.S. Appl. No. 12/457,331, filed Jun. 8, 2009, 11 pages.
Final Office Action dated Oct. 15, 2009, for U.S. Appl. No. 11/239,122, filed Sep. 30, 2005, 13 pages.
Final Office Action dated Aug. 14, 2012, for U.S. Appl. No. 13/037,089, filed Feb. 28, 2011, 14 pages.
Final Office Action dated Sep. 23, 2013, for U.S. Appl. No. 13/037,089, filed Feb. 28, 2011, 14 pages.
Hemmerich, K.J. et al. (Apr. 1995)."Guide to Engineering Thermoplastics," Medical Devices and Diagnostic Industry pp. 39-59.
International Search Report dated Dec. 3, 2004, for PCT Application No. PCT/US2004/08798, filed on Mar. 24, 2004, 3 pages.
International Search Report dated May 2, 2007, for PCT Application No. PCT/US2006/37923, filed on Sep. 9, 2006, 1 page.
International Search Report dated Aug. 16, 2007 for PCT Application No. PCT/US2006/038163, filed on Sep. 29, 2006, 1 page.
International Search Report dated on Aug. 17, 2007 for PCT/US2006/38049, filed on Sep. 29, 2006, 1 page.
International Search Report dated Oct. 19, 2012 for PCT Application No. PCT/US2012/049629, filed on Aug. 3, 2012, 4 pages.
International Search Report dated Oct. 15, 2014 for PCT Application No. PCT/US2014/043516, filed on Jun. 20, 2014, 2 pages.
International Search Report dated Jan. 16, 2008, for PCT Application No. PCT/US2006/022840, filed on Jun. 13, 2006, 1 page.
Integ. (2000). "LifeGuide™ Glucose Meter. No Lancets. No Blood," located at <http://www.integonline.com>, last visited May 1, 2000, 10 pages.
Ishii H. et al., (Aug. 2001). "Seasonal Variation of Glycemic Control in Type 2 Diabetic Patients", Diabetes Care 24(8):1503.
Massey V. et al. (Aug. 1960). "Studies on the Reaction Mechanism of Lipoyl Dehydrogenase" Biochim. Biophys. Acta 48: 33-47.
Non-Final Office Action dated Dec. 12, 2007, for U.S. Appl. No. 11/529,613, filed Sep. 29, 2006, 13 pages.
Non-Final Office Action dated Apr. 28, 2009, for U.S. Appl. No. 11/529,613, filed Sep. 29, 2006, 21 pages.
Non-Final Office Action dated Jun. 4, 2010, for U.S. Appl. No. 11/529,613, filed Sep. 29, 2006, 23 pages.
Non-Final Office Action dated Mar. 23, 2012, for U.S. Appl. No. 13/197,592, filed Aug. 3, 2011, 7 pages.
Non-Final Office Action dated Mar. 23, 2012, for U.S. Appl. No. 13/197,603, filed Aug. 3, 2011, 6 pages.
Non-Final Office Action dated Nov. 26, 2012 for U.S. Appl. No. 13/562,129, filed Jul. 30, 2012, 9 pages.
Non Final Office Action dated Apr. 8, 2015, for U.S. Appl. No. 13/566,886, filed Aug. 3, 2012, 11 pages.
Non Final Office Action dated Apr. 12, 2011, for U.S. Appl. No. 11/311,667, filed Dec. 20, 2005, 7 pages.
Non Final Office Action dated Aug. 5, 2014, for U.S. Appl. No. 13/669,366, filed Nov. 5, 2012, 8 pages.
Non Final Office Action dated Dec. 5, 2014, for U.S. Appl. No. 13/562,129, filed Jul. 30, 2012, 7 pages.
Non Final Office Action dated Jan. 12, 2009, for U.S. Appl. No. 11/529,612, filed Sep. 29, 2006, 9 pages.
Non Final Office Action dated Jan. 21, 2011, for U.S. Appl. No. 11/529,612, filed Sep. 29, 2006, 9 pages.
Non Final Office Action dated Jul. 13, 2010, for U.S. Appl. No. 12/222,724, filed Aug. 14, 2008, 11 pages.
Non Final Office Action dated Jul. 31, 2015, for U.S. Appl. No. 13/669,366, filed Nov. 5, 2012, 16 pages.
Non Final Office Action dated Mar. 21, 2014, for U.S. Appl. No. 13/562,129, filed Jul. 30, 2012, 12 pages.
Non Final Office Action dated Mar. 25, 2011, for U.S. Appl. No. 12/222,724, filed Aug. 14, 2008, 13 pages.
Non Final Office Action dated Mar. 5, 2010, for U.S. Appl. No. 11/311,667, filed Dec. 20, 2005, 8 pages.
Non Final Office Action dated May 14, 2008, for U.S. Appl. No. 11/529,612, filed Sep. 29, 2006, 9 pages.

(56) References Cited

OTHER PUBLICATIONS

Non Final Office Action dated May 16, 2013, for U.S. Appl. No. 13/669,366, filed Nov. 5, 2012, 8 pages.
Non Final Office Action dated May 5, 2005, for U.S. Appl. No. 10/131,268, filed Apr. 23, 2002, 8 pages.
Non Final Office Action dated Nov. 2, 2006, for U.S. Appl. No. 11/125,107, filed May 10, 2005, 10 pages.
Non Final Office Action dated Oct. 14, 2009, for U.S. Appl. No. 11/529,612, filed Sep. 29, 2006, 10 pages.
Non Final Office Action dated Oct. 3, 2008, for U.S. Appl. No. 10/722,074, filed Nov. 24, 2003, 10 pages.
Non-Final Office Action dated Dec. 17, 2015, for U.S. Appl. No. 11/529,614, filed Sep. 29, 2006, 6 pages.
Non Final Office Action dated Dec. 2, 2004, for U.S. Appl. No. 10/347,620, filed Jan. 22, 2003, 8 pages.
Non-Final Office Action dated Jan. 27, 2009, for U.S. Appl. No. 11/529,614, filed Sep. 29, 2006, 17 pages.
Non-Final Office Action dated Jan. 6, 2014, for U.S. Appl. No. 11/529,614, filed Sep. 29, 2006, 12 pages.
Non-Final Office Action dated Jun. 21, 2013, for U.S. Appl. No. 13/752,261, filed Jan. 28, 2013, 12 pages.
Non-Final Office Action dated Jun. 6, 2008, for U.S. Appl. No. 11/529,614, filed Sep. 29, 2006, 17 pages.
Non-Final Office Action dated Oct. 9, 2014, for U.S. Appl. No. 14/446,262, filed Jul. 29, 2014, 15 pages.
Non-Final Office Action dated Sep. 29, 2004, for U.S. Appl. No. 10/394,230, filed Mar. 24, 2003, 10 pages.
Non-Final Office Action dated Nov. 23, 2011, for U.S. Appl. No. 12/457,331, filed Jun. 8, 2009, 6 pages.
Written Opinion dated Oct. 19, 2012 for PCT Application No. PCT/US2012/049629, filed on Aug. 3, 2012, 7 pages.
Non-Final Office Action dated Jun. 25, 2015, for U.S. Appl. No. 12/457,332, filed Jun. 8, 2009, 7 pages.
Non-Final Office Action dated Jul. 8, 2015, for U.S. Appl. No. 12/457,331, filed Jun. 8, 2009, 13 pages.
Non-Final Office Action dated Aug. 19, 2015, for U.S. Appl. No. 14/311,114, filed Jun. 20, 2014, 15 pages.
Non-Final Office Action dated Mar. 19, 2009, for U.S. Appl. No. 11/239,122, filed Sep. 30, 2005, 15 pages.
Non-Final Office Action dated Sep. 1, 2010, for U.S. Appl. No. 11/239,122, filed Sep. 30, 2005, 15 pages.
Non-Final Office Action dated Sep. 13, 2011, for U.S. Appl. No. 13/037,089, filed Feb. 28, 2011, 14 pages.
Non-Final Office Action dated Feb. 28, 2013, for U.S. Appl. No. 13/037,089, filed Feb. 28, 2011, 12 pages.
Non-Final Office Action dated Apr. 10, 2014, for U.S. Appl. No. 13/037,089, filed Feb. 28, 2011, 14 pages.
Non-Final Office Action dated May 29, 2015, for U.S. Appl. No. 14/614,177, filed Feb. 4, 2015, 13 pages.
Notice of Allowance dated May 3, 2011, for U.S. Appl. No. 11/529,613, filed Sep. 29, 2006, 12 pages.
Notice of Allowance dated Mar. 27, 2015, for U.S. Appl. No. 13/562,129, filed Jul. 30, 2012, 7 pages.
Notice of Allowance dated Apr. 18, 2012, for U.S. Appl. No. 11/529,612, filed Sep. 29, 2006, 8 pages.
Notice of Allowance dated Apr. 19, 2010, for U.S. Appl. No. 29/338,117, filed Jun. 4, 2009, 4 pages.
Notice of Allowance dated Aug. 3, 2012, for U.S. Appl. No. 11/529,612, filed Sep. 29, 2006, 5 pages.
Notice of Allowance dated Jan. 14, 2010, for U.S. Appl. No. 29/338,117, filed Jun. 4, 2009, 4 pages.
Notice of Allowance dated Jun. 29, 2012, for U.S. Appl. No. 11/311,667, filed Dec. 20, 2005, 5 pages.
Notice of Allowance dated Mar. 14, 2012, for U.S. Appl. No. 12/222,724, filed Aug. 14, 2008, 7 pages.
Notice of Allowance dated Mar. 31, 2005, for U.S. Appl. No. 10/394,230, filed Mar. 24, 2003, 10 pages.
Notice of Allowance dated May 15, 2008, for U.S. Appl. No. 11/125,107, filed May 10, 2005, 7 pages.
Notice of Allowance dated May 18, 2009, for U.S. Appl. No. 29/300,934, filed May 30, 2008, 4 pages.
Notice of Allowance dated May 28, 2009, for U.S. Appl. No. 29/300,933, filed May 30, 2008, 6 pages.
Notice of Allowance dated Nov. 23, 2011, for U.S. Appl. No. 12/222,724, filed Aug. 14, 2008, 7 pages.
Notice of Allowance dated Nov. 27, 2012, for U.S. Appl. No. 11/529,612, filed Sep. 29, 2006, 5 pages.
Notice of Allowance dated Nov. 29, 2005, for U.S. Appl. No. 10/131,268, filed Apr. 23, 2002, 6 pages.
Notice of Allowance dated Oct. 12, 2011, for U.S. Appl. No. 11/529,612, filed Sep. 29, 2006, 8 pages.
Notice of Allowance dated Feb. 23, 2015, for U.S. Appl. No. 14/446,262, filed Jul. 29, 2014, 8 pages.
Notice of Allowance dated Feb. 5, 2014, for U.S. Appl. No. 13/752,261, filed Jan. 28, 2013, 9 pages.
Notice of Allowance dated Jun. 15, 2009, for U.S. Appl. No. 10/722,074, filed Nov. 24, 2003, 6 pages.
Notice of Allowance dated Mar. 2, 2016, for U.S. Appl. No. 11/529,614, filed Sep. 29, 2006, 12 pages.
Notice of Allowance dated Mar. 28, 2005, for U.S. Appl. No. 10/347,620, filed Jan. 22, 2003, 6 pages.
Notice of Allowance dated Jan. 26, 2017, for U.S. Appl. No. 12/457,331, filed Jun. 8, 2009, 7 pages.
Notice of Allowance dated Sep. 18, 2014, for U.S. Appl. No. 13/037,089, filed Feb. 28, 2011, 9 pages.
Notice of Allowance dated Feb. 16, 2016, for U.S. Appl. No. 14/614,177, filed Feb. 4, 2015, 7 pages.
Restriction Requirement dated Sep. 29, 2011, for U.S. Appl. No. 12/457,332, filed Jun. 8, 2009, 6 pages.
Restriction Requirement dated Dec. 22, 2011, for U.S. Appl. No. 12/457,332, filed Jun. 8, 2009, 6 pages.
Restriction Requirement dated Jul. 19, 2011, for U.S. Appl. No. 12/457,331, filed Jun. 8, 2009, 6 pages.
Sonntag, O. (1993). Ektachem. Dry Chemistry, Analysis With Carrier-Bound Reagents, Elsevier Science Publishers, 57 pages.
Spielman, A. et al. (2001). *Mosquito: A Natural History of Our Most Persistent and Deadly Foe*, First Edition, Hyperion, New York, NY, 3 pages. (Table of Contents Only).
Straub F.B. (Mar., 1939). "Isolation and Properties of a flavoprotien from Heart Muscle Tissue", Biochemical Journal 33: 787-792.
Tietz, N.W. (1986).Textbook of Clinical Chemistry, W. B. Saunders Company, pp. 1533 and 1556.
U.S. Precision Lens, Inc. (1983).The Handbook of Plastic Optics.
Written Opinion dated Jul. 28, 2009, for PCT Application No. PCT/US2009/003441, filed on Jun. 8, 2009, 10 pages.
Written Opinion dated Oct. 15, 2014 for PCT Application No. PCT/US2014/043516, filed on Jun. 20, 2014, 5 pages.
Written Opinion of the International Searching Authority dated Jan. 16, 2008, for PCT Application No. PCT/US2006/022840, filed on Jun. 13, 2006, 3 pages.
Written Opinion dated Dec. 3, 2004, for PCT Application No. PCT/US2004/08798, filed on Mar. 24, 2004, 4 pages.
Written Opinion dated May 2, 2007, for PCT Application No. PCT/US2006/37923, filed on Sep. 9, 2006, 5 pages.
Written Opinion dated Aug. 17, 2007 for PCT/US06/38049, filed Sep. 29, 2006, 6 pages.
Written Opinion dated Aug. 16, 2007 for PCT Application No. PCT/US2006/038163, filed on Sep. 29, 2006, 4 pages.
Final Office Action dated Jan. 20, 2016, for U.S. Appl. No. 12/457,332, filed Jun. 8, 2009, 10 pages.

\* cited by examiner

ANALYTE MONITORING METHODS AND SYSTEMS

CROSS-REFERENCE TO RELATED APPLICATIONS

This application claims priority to U.S. Provisional Application No. 61/358,825, filed Jun. 25, 2010.

FIELD

The invention described herein relates to methods, devices, arrangements and/or systems for monitoring a target analyte in a simpler, more accurate manner.

BACKGROUND

In this specification where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

Currently, commercially available glucose monitoring systems typically contain a number of separate components. Namely, separate lancing devices for creating a droplet of blood on the skin, test strips, and a meter configured to receive one test strip at a time. A test strip is inserted into the meter before or after the skin is lanced with the separate lancing device, then the strip is maneuvered into contact with the droplet of blood on the surface of the skin. The strip absorbs the blood, then the blood is analyzed by the strip/meter to determine the concentration of glucose contained therein.

Many of these devices allow people with diabetes to mark an individual glucose measurement to associate the result with a particular meal, or meal-time. For example, the meter might allow a user to, after a result is displayed on the meter, associate that result with "breakfast". If a user diligently marked their results associating them with the appropriate meal-time, then a user's health care provider may be able to analyze the data looking for trends in measurement that can be used to adjust the delivery time and dosage of any treatments provided (e.g., insulin). In current commercially available devices, this marking procedure must be initiated by the user.

It should be noted that another deficiency of current commercially available meters is that the available marking options are is imprecise. In particular, a person with diabetes will experience rises in glucose levels following the consumption of food. For a health care provider to make appropriate adjustments in treatments, they need to understand if particular results came before or following meals (pre or post-prandial). While there are some devices that allow for marking of results directly on the analyte monitor, it is also quite common to use a paper "logbook" to track individual results. However, it is not sufficient to only associate a particular result with a particular meal. Instead, in order to more accurately interpret and utilize the test results, it should be associated with a time period before or after a particular meal.

Additional problems with current technology include:

patient compliance—many patients find marking meals confusing and simply choose not to mark any meals, or worse, will mark, perhaps without even realizing it, individual results as being associated with a particular meal when in fact the test did not actually occur before or after a meal.

lack of data, or inaccurate data, can lead to less than optimal treatment plans, or even worse risk of harm to the patient if too much or too little treatment (drugs, insulin etc.) are provided.

data accuracy—it is quite easy to make mistakes in marking meals using currently commercially available meters.

the process for marking directly on the device is not intuitive, users must initiate the marking process, which typically involves the need to memorize a long system of key/button presses or a need to consult their users guide for directions.

when using paper and pencil a user can transcribe the result incorrectly, or write the result in the wrong section of the logbook. Also, such information cannot be easily transferred or shared with health care professionals.

marking a test as only generally being associated with a particular meal does not provide fully accurate, useful information.

time—people with diabetes can spend a significant amount of time searching for logbooks, or re-reading instructions to understand how to mark meals.

safety—incomplete or inaccurate data can lead to mistakes in treatment harming patients.

While certain aspects of conventional technologies have been discussed to facilitate disclosure of the invention, Applicants in no way disclaim these technical aspects, and it is contemplated that the claimed invention may encompass or include one or more of the conventional technical aspects discussed herein.

SUMMARY OF THE INVENTION

As used herein, "body fluid" encompasses whole blood, interstitial fluid, and mixtures thereof.

As used herein "integrated device" or "integrated meter" means a device or meter that includes all components necessary to perform sampling of body fluid, transport of body fluid, quantification of an analyte, and display of the amount of analyte contained in the sample of body fluid. Exemplary integrated meters are described in: U.S. Pat. Nos. 6,540,675 and 7,004,928; U.S. Patent Application Publication Nos. US 2008/0077048, US 2007/0179404, US 2007/0083131, US 2007/0179405, US 2007/0078358, and US 2007/0078313. The entire contents of each of the above-listed documents are incorporated herein by reference.

It is to be understood that reference herein to first, second, third and fourth components (etc.) does not limit the present invention to embodiments where each of these components is physically separable from one another. For example, a single physical element of the invention may perform the functions of more than one of the claimed first, second, third or fourth components. Conversely, a plurality of separate physical elements working together may perform the functions of one of the claimed first, second, third or fourth components. Similarly, reference to first, second (etc.) method steps does not limit the invention to only separate steps. According to the invention, a single method step may satisfy multiple steps described herein. Conversely, a plurality of method steps could, in combination, constitute a single method step recited herein. In addition, the steps of the method are not necessarily limited to the order in which they are described or claimed herein.

The present invention may address one or more of the problems and deficiencies of the prior art discussed above. However, it is contemplated that the invention may prove useful in addressing other problems and deficiencies, or provide benefits and advantages, in a number of technical areas. Therefore the claimed invention should not necessarily be construed as being limited to addressing any of the particular problems or deficiencies discussed herein.

The invention can be useful with any device, but is particularly applicable to analyte monitors used in a home or clinical setting such as glucose monitors. This invention is advantageous when used in conjunction with a fully integrated glucose meter. However, the invention is not so limited. The benefits and advantages of the invention can also be applied to other devices such as conventional (non-integrated) glucose meters and other self-diagnostic devices where collection of long term data and analysis of trends in data is important.

The present invention can provide one or more of the following benefits and advantages relative to current technology:

convenience of never having to look for instructions or paper log books, and the meter initiates the marking procedure, not the user. For example, according to the present invention, the results of the test can be displayed along with a reminder to mark the test as before or after a particular meal.

"screen real-estate"—size is a key factor for patients choosing a handheld analyte monitor and many of the LCD's used in these devices are created with fixed segments that are turned on or off to display relevant information. By compactly displaying all possible meal markers this invention saves space on the screen, which in turn allows for more of the screen used for other purposes and can therefore help reduce the overall size of the device.

significant increase in caregiver's confidence in data collected by the meter.

significant increase in the amount of accurate and useful data collected by user (pre and post prandial data).

improved ability to monitor/detect trends in test results.

ability to confidently adjust patient medications based on data collected by meter.

allows the meter to internally process data not available to currently used glucose monitors (e.g., a 7-day pre and/or post-meal average calculated by the meter).

accurate on-device averages of pre/post prandial results.

data once calculated by the device can easily be exported by the data management software used by healthcare professionals to pull data from patients' devices.

time/cost savings—by having the data automatically and accurately exported healthcare professionals are able to assist patients more quickly.

can provide users with information not available on conventional glucose meters.

According to one aspect, the present invention provides a method of monitoring the concentration of at least one target analyte in a sample of body fluid using a meter, the meter comprising a user interface, the method comprising: obtaining a sample of body fluid; testing the sample to determine the concentration of the at least one target analyte contained therein; and presenting the user with a reminder to associate the test with an appropriate time corresponding to before or after a particular meal using the user interface.

According to a further aspect, the present invention provides a testing device comprising: a user interface, a processor and a memory, the device constructed an arranged to provide the results of a test and substantially simultaneously provide the user with a reminder to associate the results of the test with an appropriate time before or after a particular meal, and to store the associated results in the memory.

BRIEF DESCRIPTION OF THE DRAWING FIGURES

The following description of preferred embodiments can be read in connection with the accompanying drawings in which like numerals designate like elements and in which.

DETAILED DESCRIPTION

Figure 1:
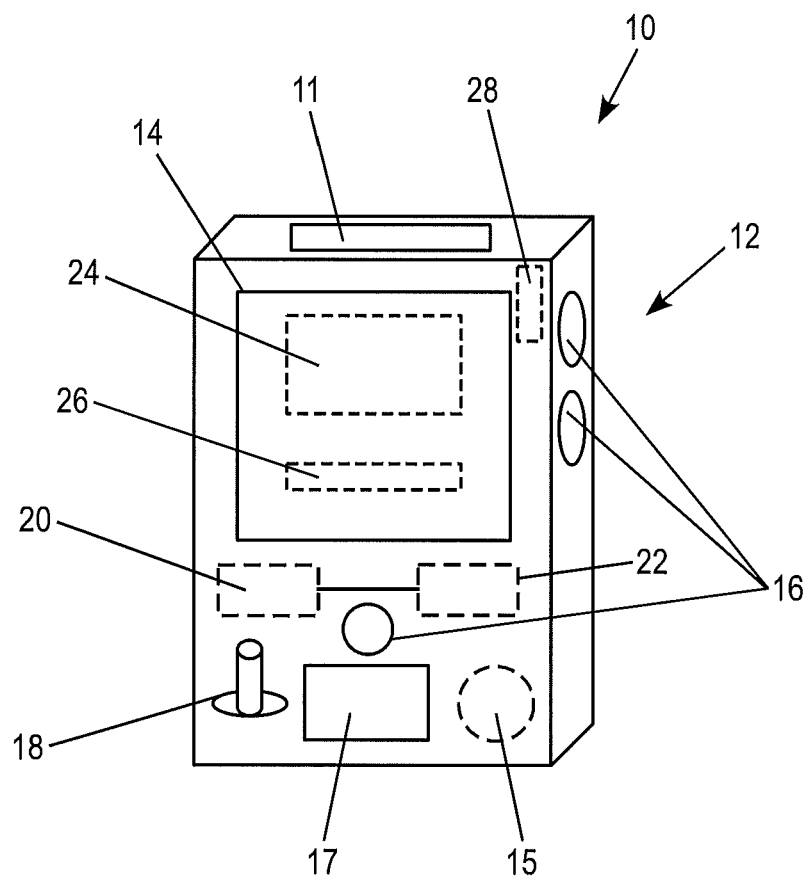
FIG. 1 is a schematic plan view of certain embodiments of the present invention.
Figure 2:
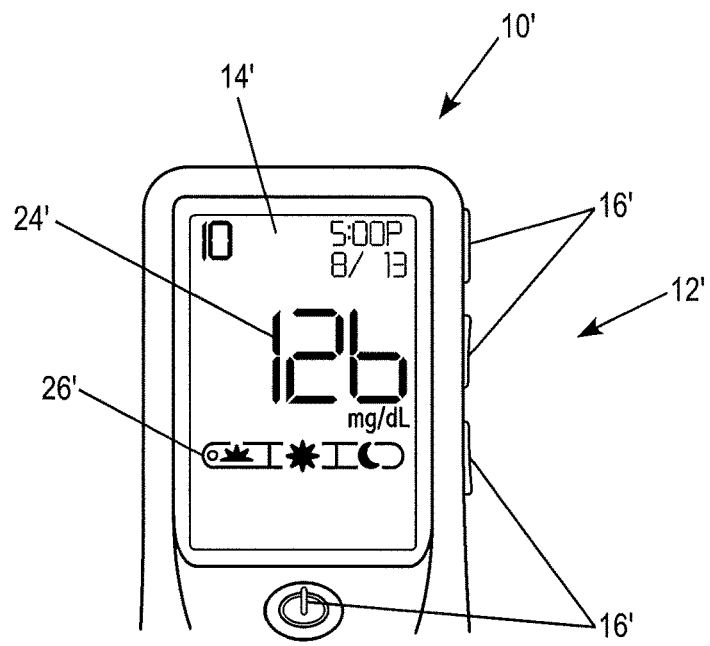
FIG. 2 is a partial plan view of certain alternative embodiments of the present invention.
Figure 3:
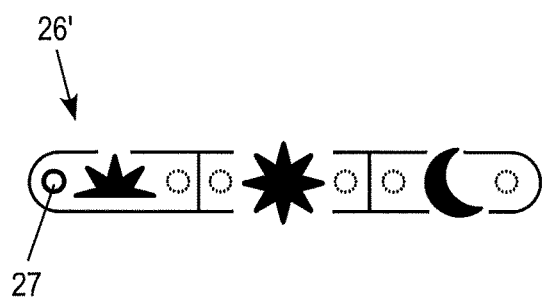
FIG. 3 is an exemplary icon used in connection with certain aspects of the present invention, designating a first marked testing time (pre-breakfast).
Figure 4:
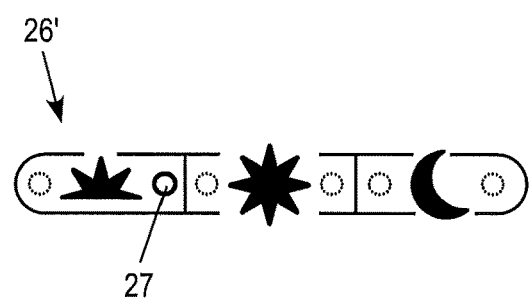
FIG. 4 is the icon of FIG. 3, designating a second marked testing time (post-breakfast).

It should be emphasized that the devices and methods described are intended to apply to any number of devices, meters or monitors. Thus, while according to certain embodiments, the principles of the present invention are applied to and used in conjunction with an integrated meter, the present invention is also usable with other devices such as conventional (non-integrated) analyte monitors. How the analyte measurement result is acquired by a particular device is not critical to implementation or practice of the present invention. The present invention is more relevant to what the device can do with results once collected. Thus, unless specifically stated to the contrary, the following description should be read as being applicable to any device, such as conventional non-integrated monitoring devices and systems, as well as integrated glucose monitors or meters. For example, when images of a display are shown or described the display could be that of any suitable device, such as a stand alone, test-strip-based device or a semi or fully integrated device. Also, the icons disclosed herein are associated with exemplary embodiments and may be changed, and still fall within the scope of the invention.

The invention provides, inter alia, an elegant and simple user interface that allows users of an analyte monitor to quickly and accurately associate a particular measurement as either pre or post-meal (pre/post-prandial).

One aspect of the invention is the functionality of a user interface that displays all possible meal time markings on a single portion of the display. Specifically, according to certain embodiments, all 6 possible meal markings are shown on the screen at one time (before or after each of breakfast, lunch, and dinner), with only one appropriate meal marker time ultimately selected. Users of the device can optionally cycle through all possible markings by interaction with an a user interface, for example, by pressing a simple up or down arrow on the side of the device or by utilizing a touch screen-type interface. Once the particular meal marker is suggested users can confirm their selection, also through interaction with the user interface, such as by pressing the power button which simultaneously marks a result and places the device into sleep mode, and/or by utilizing a touch screen-type interface.

Other aspects of the present invention involves methods or techniques for monitoring the concentration of at least one target analyte contained in a sample of body fluid. Any suitable target analyte may be monitored, such as glucose, hemoglobin, bilirubin, etc., or combinations thereof. Moreover, any suitable body fluid may be analyzed, such as saliva, urine, blood, interstitial fluid, or mixtures thereof.

As an initial step, a sample of body fluid is collected. Any suitable technique for the collection of body fluid is contemplated. For example, when the body fluid to be analyzed comprises blood, a sample can be obtained in a number of different ways. When the principles of the present invention are applied in the context of blood glucose monitoring, a sample of blood can be obtained, for example, by lancing a surface of the skin, thereby creating a wound from which a sample of blood can be obtained. Any suitable instrument can be used to create the wound, such as a solid lancet or hollow needle.

Subsequently, or concurrently, the sample is optionally transported to an appropriate analysis site, and analyzed to determine the concentration of the at least one target analyte contained therein. Any suitable technique for determining the concentration can be utilized. For example, when the principles of the present invention are utilized in the context of blood glucose monitoring, conventional electrochemical or colorimetric techniques can be utilized to ascertain the concentration of glucose contained in the sample of body fluid or blood. The results of the analysis are then presented to the user or tester. The results can be presented in any suitable manner, such as by visually displaying the results, and/or by audibly communicating the results.

According to the present invention, the user is also presented with a reminder to associate the results of the test with an appropriate time corresponding to before or after a particular meal. According to one alternative embodiment, this reminder is presented at approximately the same time as the results of the test are presented to the user. However, it should be recognized that this reminder can be provided at any suitable time so long as the user is reminded in adequate time to mark the results of the test in the desired fashion. This reminder can be presented to the user in any suitable manner. For instance, the reminder may be visually presented on a display, and/or by audibly communicating a reminder. When the reminder is visually presented on a display, any suitable symbol or combination of symbols can be utilized to communicate to the user that they should associate the test results with an appropriate time before or after a particular meal. According to one optional embodiment, an icon is displayed which contains a combination of symbols representative of all desired possible marking times. According to a further optional embodiment, an icon is displayed comprising symbols corresponding to breakfast (e.g., rising sun), lunch (e.g., midday sun), and dinner (e.g., moon), and the icon further comprises a selectable portion which can be selectively associated with an appropriate time before or after one of the above-mentioned meals. The selectable portion of the icon can be associated with an appropriate time by any suitable manner. Thus, according to certain optional embodiments, the selectable portion can be located appropriately by use of an interface device, such as one or more buttons, touch pads, touch screen, joysticks, and the like. Optionally, the selectable portion of the icon can be associated by using voice or audible commands in conjunction with voice/audible command recognition capabilities.

Further alternative embodiments include suggesting to the user an appropriate marking time for the just-completed test, based upon the time of day at which the test has been taken. For example, if the user completes a test at 6:30 AM it may be automatically suggested to the user that the test be marked as pre-breakfast. The automatic suggestion is again based upon the time of day, and optionally upon additional input which is preprogrammed and/or provided by the user. Thus, a device or mechanism can be provided which is preprogrammed to suggest that any test performed at 6:30 AM or earlier be suggested for marking as a pre-breakfast test. Alternatively, or in addition thereto, the user may customize this suggestion. For example, the user can specify that any test performed prior to 7 AM be suggested for marking as a pre-breakfast testing event.

Once the results of a particular test have been associated with an appropriate time before or after a particular meal, both the results of the test and the specified time association information is stored in any suitable manner using any suitable media. For example, the information can be stored as binary information in a memory device. According to certain embodiments, the information is stored in a format that is easily retrieved, shared and analyzed.

Further aspects of the present invention involves devices, systems, arrangements and the like which embody any or all of the above-mentioned functionality. Illustrative embodiments of such devices, systems and arrangements are described herein in connection with reference to FIGS. 1-5.

FIG. 1 illustrates an exemplary device 10. The device 10 is capable of determining the concentration of at least one target analyte contained in a sample of body fluid. Any suitable target analyte may be monitored, such as glucose, hemoglobin, bilirubin, etc., or combinations thereof. Moreover, any suitable body fluid may be analyzed, such as saliva, urine, blood, interstitial fluid, or mixtures thereof. As previously mentioned herein, such devices 10 can take a number of different forms. Thus, the device 10 can comprise an analyte monitor or meter that is designed to be used in conjunction with non-integrated systems. Thus, for example, the device 10 can be configured to cooperate with one or more of a separate test strip(s) and/or separate body fluid production/collection device(s). When configured in this manner, the device 10 can optionally include a slot or opening 11 which is configured to receive a separate test strip or cartridge therein, as previously mentioned above. When the device 10 is in the form of an integrated meter or monitor, it includes mechanisms for obtaining a sample of body fluid, analyzing the sample of body fluid, and presenting the results of the analysis, all within a single self-contained unit. Suitable integrated devices are mentioned herein, and the specifics of such constructions and modes of operation are described in the documents incorporated by reference herein.

The illustrated device 10 may include a suitable user interface 12. Alternatively, the interface can be provided separate from the device 10. For example, the device 10 may include all features necessary for analyzing a sample to determine the concentration of a target analyte contained therein, and be connected with a wired or wireless connection to a separate or remote interface, such as a display. The user interface 12 can include a display 14. Any suitable display is contemplated. According to one optional embodiment, the display 14 comprises an LCD. The user interface 12 may additionally include further components or features for interacting with a user. Thus, the user interface 12 may optionally include an audible input/output device 15, which may be in the form of a speaker and/or microphone. Additional components or features of the user interface 12 may optionally include input devices such as one or more of: buttons 16, touch pad 17, joystick 18, or any combination thereof. According to another optional construction encompassed by the above-described interface and display, the display 14 may also comprise a touch screen-type interface. According to further alternative aspects, the user interface 12 of the device 10 can include audible/voice recognition capabilities. For example, a user can interact with the device 10 by speaking or providing audible input via the audible input/output device 15, which are then interpreted and converted by the device into executable commands.

The device 10 may further be provided with a memory component 20 and a processor 22, which are operatively interconnected. Such components can be used according to generally known techniques to control the storage, manipulation and/or retrieval of information, as well as controlling, and responding to, the various components of the user interface 12.

The device 10 may include one or more sample transport features and/or analysis site comprising mechanisms for determining the concentration of at least one target analyte contained in the sample. For example, when the principles of the present invention are utilized in the context of blood glucose monitoring, conventional electrochemical or colorimetric mechanism can be included in the device 10 to ascertain the concentration of glucose contained in the sample of body fluid or blood. Examples of such mechanisms are described in greater detail in the documents incorporated herein by reference, and as previously pointed out, are not critical to practice the concepts of the present invention. The device 10 then presents the results of the analysis to the user. The results can be presented in any suitable manner, such as by visually displaying the results 24 on the display 14, and/or by audibly communicating the results via the audible input/output device 15.

According to the present invention, the device 10 also presents the user with a reminder to associate the results of the test with an appropriate time corresponding to before or after a particular meal. According to one alternative embodiment, this reminder is presented at approximately the same time as the results of the test are presented to the user. However, it should be recognized that this reminder can be provided at any suitable time so long as the user is reminded in adequate time to mark the results of the test in the desired fashion. This reminder can be presented to the user in any suitable manner. For instance, the reminder 26 may be visually presented on the display 14, and/or by audibly communicating a reminder via the audible input/output device 15. When the reminder 26 is visually presented on a display 14, any suitable symbol or combination of symbols can be utilized to communicate to the user that they should associate the test results with an appropriate time before or after a particular meal. According to one optional embodiment, the reminder 26 comprises an icon that is displayed which contains a combination of symbols representative of all desired possible marking times. According to a further optional embodiment, the reminder 26 comprises an icon is having symbols corresponding to breakfast (e.g., rising sun), lunch (e.g., midday sun), and dinner (e.g., moon), and the icon further comprises a selectable portion (e.g., 26', FIGS. 2-5) which can be selectively associated with an appropriate time for or after one of the above-mentioned meals. The selectable portion of the icon can be associated with an appropriate time by any suitable manner. Thus, according to certain optional embodiment, the selectable portion can be located appropriately by use of an interface device, such as one or more buttons 16, touch pads 17, touch screens 14, joysticks 18, and the like. Optionally, the selectable portion of the icon can be associated by using voice or audible commands via audible input/output device 15, in conjunction with voice/audible recognition capabilities possessed by the device 10.

The device 10 may further include the capability to suggest to the user an appropriate marking time for the just-completed test, based upon the time of day at which the test has been taken. For example, the device 10 is provided with a clock 28. The clock 28 can be manually set by the user, or may be automatically set and/or adjusted by any suitable mechanism. Such a device incorporating an automatic clock is disclosed in US 2010-0021948, the entire contents of which is incorporated herein by reference. In either case, if the user completes a test at 6:30 AM, the device 10 may suggest to the user via the user interface 12, in any manner described herein, to mark the test as pre-breakfast. The automatic suggestion is again based upon the time of day, and optionally upon additional input which is preprogrammed or provided by the user. Thus, the device 10 can be preprogrammed (e.g., factory programmed) to suggest that any test performed at 6:30 AM or earlier be suggested for marking as a pre-breakfast test. Alternatively, or in addition thereto, the user may customize this suggestion. For example, the user can program the device 10 to specify that any test performed prior to 7 AM be suggested for marking as a pre-breakfast testing event.

Once the results of a particular test have been associated with an appropriate time before or after a particular meal, both the results of the test and the specified time association information is stored in any suitable manner using any suitable media, such as the memory 20. For example, the information can be stored as binary information in the memory device 20. According to certain embodiments, the information is stored in a format that is easily retrieved, shared and analyzed.

A device constructed according to further alternative embodiments, and associated methods, are illustrated and described in connection with FIGS. 2-5. It should be understood that this embodiment may include any or all of the previously described functionality and/or features of the previously described embodiments.

The device 10' illustrated therein can be in the form of an integrated monitor or meter. Thus, it may possess any or all of the features associated with such integrated monitors, and as described in the documents incorporated by reference herein. In addition, the previously described principles of the present invention, when applied to such an integrated device 10', possesses numerous benefits and advantages, as generally described herein.

As with the previously described embodiments, the device 10' optionally includes a user interface 12' associated with the device 10'. The user interface 12' can include a number of features, such as a display 14', which may also comprise a touch-screen-type interface, and/or one or more buttons 16'. Upon analysis of a suitable sample of body fluid, the device 10' analyzes the sample and determines the concentration of at least one target analyte contained therein. These results are then presented to the user. According to the illustrated embodiment, the results 24' are presented to the user by displaying them on the display 14'. The electronics, and interactions therewith necessary to accomplish this display functionality is generally well-known to those in the art, and is not critical practice the principles of the present invention. In addition, the device 10' presents a reminder to the user to associate the results 24' with an appropriate time before or after a particular meal. The device 10' can present this reminder in any suitable manner. According to the illustrated embodiment, the reminder is presented on the display 14' in the form of an icon 26'. The icon 26' can comprise any suitable symbol or combination of symbols to communicate to the user that they should associate the test results with an appropriate time before or after a particular meal. According to the illustrated embodiment, the icon 26' contains a combination of symbols representative of all desired possible marking times. Further, the illustrated embodiment comprises symbols corresponding to breakfast (e.g., rising sun), lunch (e.g., midday sun), and dinner (e.g., moon), and the icon 26' further comprises a selectable portion 27 which can be selectively associated with an appropriate time before or after one of the above-mentioned meals. The selectable portion 27 of the icon can be associated with an appropriate time/meal by any suitable manner. Thus, according to certain optional embodiments, the selectable portion 27 can be located appropriately by use of an interface device, such as one or more buttons 16', or a touch screen 14'. As with the previously described embodiments, the selectable portion 27 can be manipulated with alternative interface devices such as, touch pads, touch screens, joysticks, and audible commands, which may optionally form part of the device 10'.

The device 10' may optionally further include the previously described features and functionality associated with suggesting an appropriate time marking to the user based upon the time of day at which the test is conducted. The device 10' may optionally utilize a manually set or automated clock, as previously described.

Figure 5:
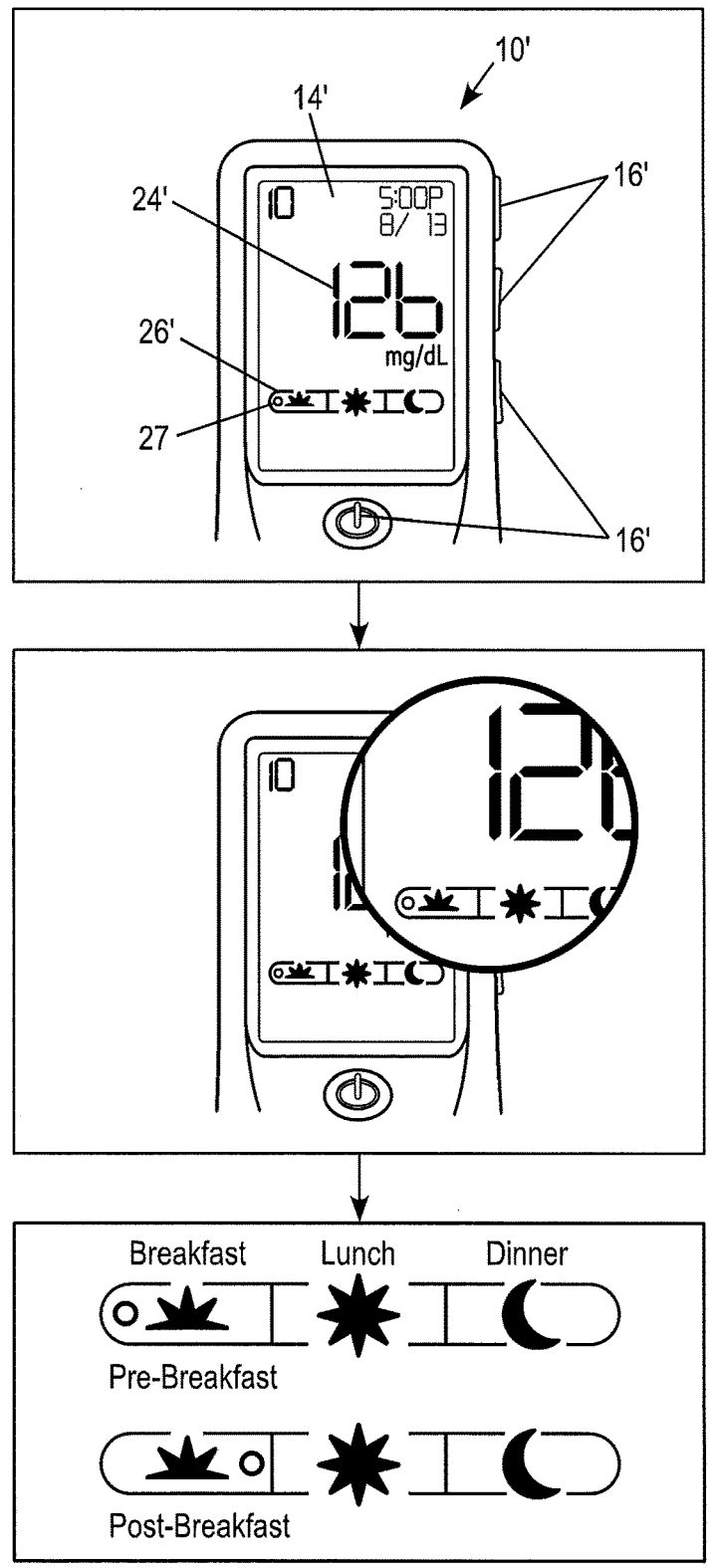
FIG. 5 is an illustration of a method or technique of the present invention, optionally Used in conjunction with the device of FIG. 2.

One possible mode of operation of the device 10' is illustrated in FIG. 5. The integrated device 10' is utilized in a known manner to produce and collect a sample of body fluid, transport the sample to an appropriate analysis site within the device 10', and analyzed a sample to determine the concentration of a target analyte contained therein. Once this analysis has been performed, the results 24' are presented to the user on the display 14'. According to the illustrated embodiment, a reminder to mark the results as associated with an appropriate time before or after a particular meal is also displayed or presented to the user at substantially the same time as the display of the results 24'. Although it is contemplated that the reminder may be presented at a time which is before or after presentation of the results, as previously noted herein. According to the illustrated embodiment, the reminder is in the form of an icon 26'. The icon 26' contains a combination of symbols representing breakfast, lunch and dinner. The icon 26' further includes a selectable portion 27 for associating the results of the test with a time before or after a particular meal. The selectable portion 27 is optionally suggested to the user based at least in part upon the time of day at which the test is conducted as indicated by the clock 28 of the device 10'. According to one alternative, the selectable portion 27 flashes in the suggested location. Regardless of whether an appropriate marking is suggested by the device 10', the user may change the position of the selected portion by using any suitable interface, such as the buttons 16' of the device 10', or by a touch screen 14'. Thus, according to the illustrated embodiment, should the user agree with the suggested marking, the user can make the selection by any suitable means, such as by simply pressing the power button to confirm that this is the appropriate time marking for the testing event. If the user wishes to deviate from the suggested marking position, or independently select an appropriate marking position for the selectable portion 27 of the icon 26', the user can change the position of the selectable portion 27 by use of one or more of the buttons 16' of the device 10', or by utilizing a touch screen 14'. Again, once the user is satisfied with the appropriate positioning of the selectable portion 27, the choice is confirmed (e.g., by pushing the power button), and the procedure is completed. The device 10' then stores the results along with the associated time information in a memory 20 of the device 10', which can then be retrieved and analyzed either with by the device itself 10', or by external devices (not shown).

Numbers expressing quantities of ingredients, constituents, reaction conditions, and so forth used in this specification are to be understood as being modified in all instances by the term "about". Notwithstanding that the numerical ranges and parameters setting forth, the broad scope of the subject matter presented herein are approximations, the numerical values set forth are indicated as precisely as possible. Any numerical value, however, may inherently contain certain errors necessarily resulting from the standard deviation found in their respective measurement techniques. None of the elements recited in the appended claims should be interpreted as invoking 35 U.S.C. § 112, 116, unless the term "means" is explicitly used.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

We claim:

1. A method comprising:
presenting the user with a reminder to associate an analyte test result with an appropriate time corresponding to before or after a meal using a meter comprising a user interface, wherein presenting the reminder comprises displaying an icon on the user interface, wherein the icon comprises a plurality of symbols and a meal time indicator, wherein each symbol corresponds to a different meal and the meal is either breakfast, lunch, or dinner, and the meal time indicator is moveable between a pre-meal position for each meal and a post-meal position for each meal.

2. The method of claim 1, wherein the meter comprises an integrated meter.

3. The method of claim 1, wherein the user interface comprises a display.

4. The method of claim 3, wherein the user interface comprises a mechanism for presenting an audible signal to the user.

5. The method of claim 1, wherein the method further comprises piercing skin of the user thereby creating a wound, and receiving a sample of body fluid from the wound.

6. The method of claim 5, further comprising transporting the sample of body fluid to an analysis site within the meter.

7. The method of claim 1, wherein presenting the user with a reminder further comprises producing an audible signal.

8. The method of claim 1, wherein the plurality of symbols comprises symbols that correspond to breakfast, lunch, and dinner.

9. The method of claim 1 further comprising:
receiving user input regarding a position of the meal time indicator of the icon, thereby associating the analyte test result with an appropriate time corresponding to a time before or after a meal.

10. The method of claim 1, wherein the user interface comprises a display, and the method further comprises displaying the analyte test result, and substantially simultaneously displaying the reminder to associate the analyte test result with an appropriate time corresponding to before or after a meal.

11. The method of claim 1, wherein the meter comprises a clock, and wherein when presenting the user with the reminder, the meter suggests a position of the meal time indicator of the icon based upon the time of day indicated by the clock.

12. The method of claim 11 further comprising receiving confirmation of the suggested position, or receiving instructions to move the meal time indicator to a different position in the icon.

13. The method of claim 9, wherein association thereof associating the analyte test result with an appropriate time corresponding to before or after a meal generates data, and wherein the meter comprises a memory, and the method further comprises storing the data in the memory.

14. The method of claim 13, further comprising exporting the data from the meter.

15. The method of claim 14, further comprising exporting the data to heath care management software.

16. The method of claim 14, further comprising automatically exporting the data from the meter without user intervention.

17. The method of claim 1 further comprising associating the analyte test result with an appropriate time before or after a meal and storing the analyte test result in a memory, wherein the analyte test result is associated with the appropriate time before, after, or concurrently with storing the analyte test result in the memory.

18. The method of claim 17 further comprising receiving instructions to associate a stored analyte test result with the appropriate time via the user interface of the meter.

19. The method of claim 18, wherein the user interface comprises a display and at least one control.

20. The method of claim 19, wherein the at least one control comprises at least one of: a button, a joystick, a touchpad, a touch screen, or a trackball, or combinations thereof.

21. The method of claim 17, wherein the meter automatically associates the analyte test result with the appropriate time before or after a meal.

22. A testing device comprising:
a user interface;
a non-transitory memory comprising instructions to:
provide the user with a reminder via the user interface to associate an analyte test result with an appropriate time before or after a meal, wherein the reminder comprises an icon and the icon comprises a plurality of symbols and a meal time indicator, wherein each symbol corresponds to a different meal and the meal is either breakfast, lunch, or dinner, and the meal time indicator is moveable between a pre-meal position for each meal and a post-meal position for each meal; and
store the associated analyte test result in the memory; and
a processor programmed to carry out the instructions on the non-transitory memory.

23. The device of claim 22, wherein the user interface comprises a display.

24. The device of claim 22, wherein the device comprises a mechanism for producing an audible signal to the user.

25. The device of claim 22, wherein the testing device comprises a meter configured to determine a concentration of at least one target analyte contained in a sample of body fluid.

26. The device of claim 25, wherein the analyte comprises glucose and the body fluid comprises blood.

27. The device of claim 26, wherein the meter comprises an integrated meter configured to collect the sample of body fluid from the user, test the sample to determine the concentration of target analyte contained therein, and present the analyte test result to the user, all in a single unitary device.

28. The device of claim 27, the device further comprising an analysis site and a mechanism for transporting the sample of body fluid to the analysis site within the meter.

29. The device of claim 22, wherein the plurality of symbols comprises symbols that correspond to breakfast, lunch, and dinner.

30. The device of claim 22, wherein the user interface comprises a mechanism for selecting or confirming the position of the meal time indicator of the icon to associate the analyte test result with an appropriate time corresponding to a time before or after breakfast, lunch, or dinner.

31. The device of claim 22, wherein the meter comprises a clock, and wherein the non-transitory memory further comprises instructions to, when providing the user with a reminder, suggest an appropriate position of the meal time indicator of the icon based upon the time of day indicated by the clock.

32. The device of claim 30, wherein the mechanism comprises at least one of: a button, a joystick, a touchpad, a touch screen or a trackball, or combinations thereof.

33. The method of claim 8, wherein the symbol that corresponds to breakfast is an image of a rising sun and the symbol that corresponds to dinner is an image of a moon.

34. The method of claim 33, wherein the symbol that corresponds to lunch is an image of a midday sun.

35. The device of claim 29, wherein the symbol that corresponds to breakfast is an image of a rising sun and the symbol that corresponds to dinner is an image of a moon.

36. The device of claim 35, wherein the symbol that corresponds to lunch is an image of a midday sun.

* * * * *